(12) United States Patent
Sherwood et al.

(10) Patent No.: US 7,739,075 B2
(45) Date of Patent: Jun. 15, 2010

(54) METHOD FOR COMPUTING CRYSTAL SHAPES FROM X-RAY DIFFRACTION DATA (XRD) OF A SUBSTANCE

(75) Inventors: Daniel Sherwood, Karaikudi (IN); Bosco Emmanuel, Karaikudi (IN)

(73) Assignee: The Council of Scientific and Industrial Research, New Delhi (IN)

( * ) Notice: Subject to any disclaimer, the term of this patent is extended or adjusted under 35 U.S.C. 154(b) by 1106 days.

(21) Appl. No.: 11/396,163

(22) Filed: Mar. 31, 2006

(65) Prior Publication Data

US 2007/0168130 A1     Jul. 19, 2007

(30) Foreign Application Priority Data

Mar. 31, 2005    (IN)    ........................ 733/DEL/2005

(51) Int. Cl.
    *G01B 5/02*      (2006.01)
(52) U.S. Cl. ............................. 702/172; 702/1; 702/22; 378/70; 378/73
(58) Field of Classification Search ...................... 702/1, 702/22, 27, 28, 127, 155, 156, 166, 170, 702/172; 73/865.5, 865.8, 866; 378/1, 51, 378/54, 70, 71, 73, 74
See application file for complete search history.

(56) References Cited

U.S. PATENT DOCUMENTS 6,345,235 B1 *   2/2002   Edgecombe et al. .......... 702/27

OTHER PUBLICATIONS

Miao et al., "High resolution 3D X-ray Diffraction Microscopy," Phys Rev Lett., vol. 89, No. 8, Aug. 19, 2002. pp. 088303-1/4.*
Sherwood et al., "Computing shapes of nanocrystals from X-ray diffraction data," Crystal growth & Design, vol. 6, No. 6 (2006).*
Miao et al, "High resolution 3D X-ray diffraction microscopy." Phys Rev. Lett (2002).*
Cullity, Elements of X-ray diffraction, Addision-Wesley, Massachusetts, (1956).*
Chang et al., "Atomic structures by direct transformation of diffraction patterns," J. Of Physics and Chemistry of solids, 62 (2001).*
Chen et al., "Homogenous precipitation of cerium dioxide nanoparticles in alcohol/water mixed solvents." Colloids and Surfaces a: Physicochemical and Engineering Aspects, vol. 242, pp. 61-69, Jun. 2004.
Curtis et. al, "Preparation and Characterization of LiMn$_2$O$_4$ Spinel Nanoparticles as Cathode Materials in Secondary Li Batteries," Journal of the Electrochemical Society, vol. 151 No. 4, pp. A590-A598, Feb. 2004.

(Continued)

*Primary Examiner*—Drew A Dunn
*Assistant Examiner*—Hyun Park
(74) *Attorney, Agent, or Firm*—Knobbe Martens Olson & Bear LLP

(57) ABSTRACT

The present invention relates to a method for computing external crystal shapes from X-Ray Diffraction Data (XRD) of a substance. Each diffraction peak arises from a set of crystal planes and the peak width is related to the thickness of the crystal in a direction perpendicular to these set of planes. The crystal shape is actually given by the mathematical envelope of the pairs of planes corresponding to each diffraction peak.

18 Claims, 16 Drawing Sheets

OTHER PUBLICATIONS

Gehin et al., "Synthesis of Fe(II-III) hydroxysulphate green rust by coprecipitation." Solid State Science, vol. 4, pp. 61-66, Jan. 2002.

Hwang et al., "Synthesis and characterization of nanocrystalline ZnO powders by a novel combustion synthesis method." Materials Science and Engineering B, vol. 111, pp. 197-206, Jul. 2004.

Kitayama et. al, "The Wulff Shape of Alumina: III, Undoped Alumina." J. Am. Ceram. Soc., vol. 85, No. 3, pp. 611-622, Mar. 2002.

Kotarba et al., "Modification of Electronic Properties of $Mo_2C$ Catalyst by Potassium Doping: Impact on the Reactivity in hydrodenitrogenation Reaction of Indole." J. Phys. Chem. B, vol. 108, pp. 2885-2892, Apr. 2004 and figure 2.

Liu, C., "Polyol Process Synthesis of Monodispersed FePt Nanoparticles." J. Phys. Chem. B, vol. 108 No. 20, pp. 6121-6123, Apr. 2004.

Mahday et al., "Mechanically induced solid state carburization for fabrication of nanocrystalline ZZrC refractory material powders." Journal of Alloys and Compounds, vol. 299, pp. 244-253, Feb. 2000.

Tsai et al, "A Stable Quasicrystal in Al-Cu-Fe System." Japanese Journal of Applied Physics, vol. 26 No. 9, pp. L1505-L1507, Sep. 1987; see also figure 3.

Wang et al., "Synthesis of Germanium Nanocubes by a Low-Temperature Inverse Micelle Solvothermal Technique." Langmuir, vol. 21, pp. 751-754, Dec. 2004.

Yang, X., "Thermal nitridation synthesis of MN (M = Ti, V and Cr) nanocrystals from metals and $NH_4Cl$." Materials Research Bulletin, vol. 39, pp. 957-962, Apr. 2004.

Zeng et al., "Shape-Controlled Synthesis and Shape-Induced Texture of $MnFe_2O_4$ Nanoparticles." J.Am. Chem. Soc., vol. 126, pp. 11458-11459, Aug. 2004.

Zhao et al., "Synthesis and Characterization of Single-Crystalline $IN_2O_3$ Nanocrystals via Solution Dispersion." Langmuir, vol. 20, pp. 27-29, Dec. 2003.

\* cited by examiner

METHOD FOR COMPUTING CRYSTAL SHAPES FROM X-RAY DIFFRACTION DATA (XRD) OF A SUBSTANCE

CROSS-REFERENCE TO RELATED APPLICATIONS

This application claims the benefit of India Application No. 0733/DEL/2005 filed Mar. 31, 2005, which is hereby incorporated by reference in its entirety.

FIELD OF THE INVENTION

The present invention relates to a method for computing external crystal shapes from X-Ray Diffraction Data (XRD) of a substance.

BACKGROUND OF THE INVENTION

Crystal shape/habit/morphology is an important characteristic of crystals (both single crystal and powder specimen) which determines several functional properties and hence their applications. The crystal shape information consists of:
1) The number and types of crystal faces exposed
2) The geometrical area of each exposed crystal face
3) The relative orientation of adjacent crystal faces
4) The volume of the crystal and
5) The 3-D shape of the crystal.

After the discovery of X-rays in 1895 by W. C. Roentgen, X-ray crystallography was developed into a remarkably useful methodology finding applications in a wide variety of areas such as minerals/ores/geology, solid state physics and chemistry, materials science, environmental and pharmaceutical industries, to name a few.

The three-dimensional structure of non-amorphous materials, such as minerals, is defined by regular, repeating planes of atoms that form a crystal lattice. When a focused X-ray beam interacts with these planes of atoms, part of the beam is transmitted, part is absorbed by the sample, part is refracted and scattered and part is diffracted. X-rays are diffracted by each mineral differently depending on what atoms make up the crystal lattice and how these atoms are arranged.

There are two major types of X-ray Diffractometers: single crystal diffractometer and powder diffractometer. As the name suggests, the first kind examines a single crystal of size ranging from centimeters down to micro-meters and even nano-meters. Powder diffractometers use powder specimens which consist of a large number of tiny particles which are either small single crystals or agglomerates of them, the size of these particles ranging usually from micro-meters to nano-meters.

Very sophisticated X-Ray diffraction machines are available today to aid in the study of materials. Examples of the output from the X-ray diffractometer are shown in FIG. 1 [J. Phys. Chem. B, 108, 2887, 2004] and FIG. 2 [J. Phys. Chem. B, 108, 6121, 2004]. What is shown is called an X-ray diffraction pattern and it consists of a series of well-defined peaks at different $2\theta$-values, where $\theta$ is the angle of incidence of the X-ray. The positions of these peaks are described by the Bragg formula [C. Hammond, The Basics of Crystallography and Diffraction, Oxford Science, New York, 2001].

$$2d \sin \theta = n\lambda$$

where
$\lambda$=wave-length of X-ray used (Å)
n=order of the diffraction
$\theta$=angle of incidence of the X-ray (degrees)
d=inter-planar spacing along a given crystal direction (Å).

In addition to the position of the diffraction peaks on the 2-axis, the intensity of the diffraction given by the height of the peak and the peak broadening as measured by the width (B) of the peak at half the peak-height are important variables used in the analysis and interpretation of the X-ray diffraction data. In particular, the Scherrer formula [B. D. Cullity, Elements of X-ray Diffraction, Addison-Wesley, Massachusetts, 1956]

$$t_{hkl} = 0.9 * \lambda / (B \cos \theta_{hkl})$$

where
$\lambda$=wave-length of X-ray used.
$\theta_{hkl}$=angle of incidence of X-ray on the planes with Miller indices (h, k, l).
B=peak-width at half-maximum.
$t_{hkl}$=thickness of crystal perpendicular to (h, k, l) planes.
is worthy of quote in this context.

A wide range of information may be culled out from XRD patterns using a set of well-developed theoretical/mathematical frame-works. A popular and routine application of an XRD pattern is the identification (also known as characterization) of materials [B. D. Cullity, Elements of X-ray Diffraction, Addison-Wesley, Massachusetts, 1956];

Such an application merely involves a comparison of the XRD pattern of the substance of interest with a library of the XRD patterns of standard reference substances and matching the patterns. This library goes under the name of ICDD (or formerly JCPDS) [www.iucr.ac.uk] data files. More involved analyses of the XRD data will consist in the use of mathematical algorithms and softwares. For example, the internal structure of crystals, consisting of the unit cell parameters (a, b, c and $\alpha$, $\beta$, $\gamma$), the atomic/ionic positions within the unit cell and the space-group symmetries, is normally elucidated using fairly advanced mathematical procedures such as the Rietveld refinement [www.bgmn.de for more details].

Though the internal crystal structure determination is the single most prominent application of XRD, there are several other applications to which a mention should be made: qualitative & quantitative chemical analyses, phase purity, phase-diagrams, order-disorder transitions and even mechanical stress.

It must be mentioned that the internal crystal structure of crystals is different from the external physical shapes of crystals which usually goes under the names crystal shape/morphology/habits [F. C. Philips, An Introduction to Crystallography, Longmans, Glasgow, 1971].

Crystal shape is the first thing to come to mind when we think of crystallography (morphology and habits are terms related to the crystal shape). There have been several early attempts to relate the internal structure/symmetry of crystals to crystal shapes/habits. Soon it was realized that there was no straight and quantitative relation which applies to all crystals. Further, the external environment during crystallization plays an important role in determining the shape of particular crystals. For example, there are marked differences of habit for crystallization from vapor and from melt. As Gibbs postulated half a century ago, the physical process of crystal growth is one in which energy factors must be important, i.e. the equilibrium shape of a crystal would be one of minimum total surface free energy for a given volume (Wulff's construction [K. Oura et al., Surface Science An Introduction, Spinger-Verlag, New York, 2003; M. Kitayama et. al., J. Am. Ceram. Soc., 85, 611, 2002]). For kinetically controlled crystal growth, the rates of growth of different faces determine the final crystal shape. It is well known that in kinetically controlled crystal growth fast-growing faces grow "out" of the crystal and disappear, leaving the slow-growing faces to determine the crystal shape. In thermodynamically controlled crystal growth, faces with smaller surface energies dominate the crystal shape. Further, the solvent and other additives may bring about their own "medium effects" by promoting or blocking growth on particular crystal faces.

Traditionally the crystal shape information is gathered from optical microscopes and goniometers [F. C. Philips' book cited above], Scanning electron microscopes (SEM) [A. P. Tsai et al, Japanese Journal of Applied Physics, 26, 1505, 1987; see also FIG. 3], Transmission electron microscopes (TEM/HRTEM) [Calvin J. Curtis et. al, Journal of The Electrochemical Society, 151, A590, 2004], scanning tunneling microscopes (STM) [K. Oura et al., Surface Science An Introduction, Spinger-Verlag, New York, 2003] and the likes, depending on the size of crystal particles. While the optical microscopes and goniometers are used for large crystals (from microns up to centimeters), sub-microns are amenable to the more advanced TEM, HRTEM etc. However, nanocrystal shapes are not easily obtainable from any of these.

It is further noted here that a set of crystal drawing methods exists which draw crystal shapes based on data gathered from goniometers [F. C. Philips' book cited above]. However, goniometers are useful only for macro-sized crystals, whereas the present method applies to micro and nano-sized crystals. [www.shapesoftware.com].

Using equipment such as TEM and HRTEM only qualitative information can be gathered from the visual micrographs or photographs taken by these equipments, without further analysis. In addition, assigning each of the crystal faces to an unique miller index (h, k, l) is not possible. These equipments provide only projected 2D information and not 3D information about the crystal shape. Hence, one cannot view the crystal from arbitrary angles and besides only the crystal faces exposed to the instrument's camera will be accessible for inspection. Equipments like TEM and HRTEM are not only costlier than XRD but also not as common as the latter.

SUMMARY OF THE INVENTION

An aspect of the present invention is to provide a method for computing crystal shapes from X-Ray Diffraction Data (XRD) of a substance.

Another aspect of the present invention is to provide a method for computing crystal shapes from X-Ray Diffraction Data (XRD) of a substance useful to generate the external shape of the crystals.

Embodiments of the present invention provide a method for computing crystal shapes from X-Ray Diffraction Data (XRD) of a substance useful to generate the external shape of the crystals. Each diffraction peak arises from a set of crystal planes and the peak width is related, through Scherrer formula, to the thickness of the crystal in a direction perpendicular to these set of planes and realizing that the crystal shape is actually given by the mathematical envelope of the pairs of planes corresponding to each diffraction peak. The distance of separation of the two planes in the pair is related to the peak width. A mathematical algorithm is provided to compute this envelope and the related crystal shape information.

DETAILED DESCRIPTION OF THE INVENTION

Figure 1:
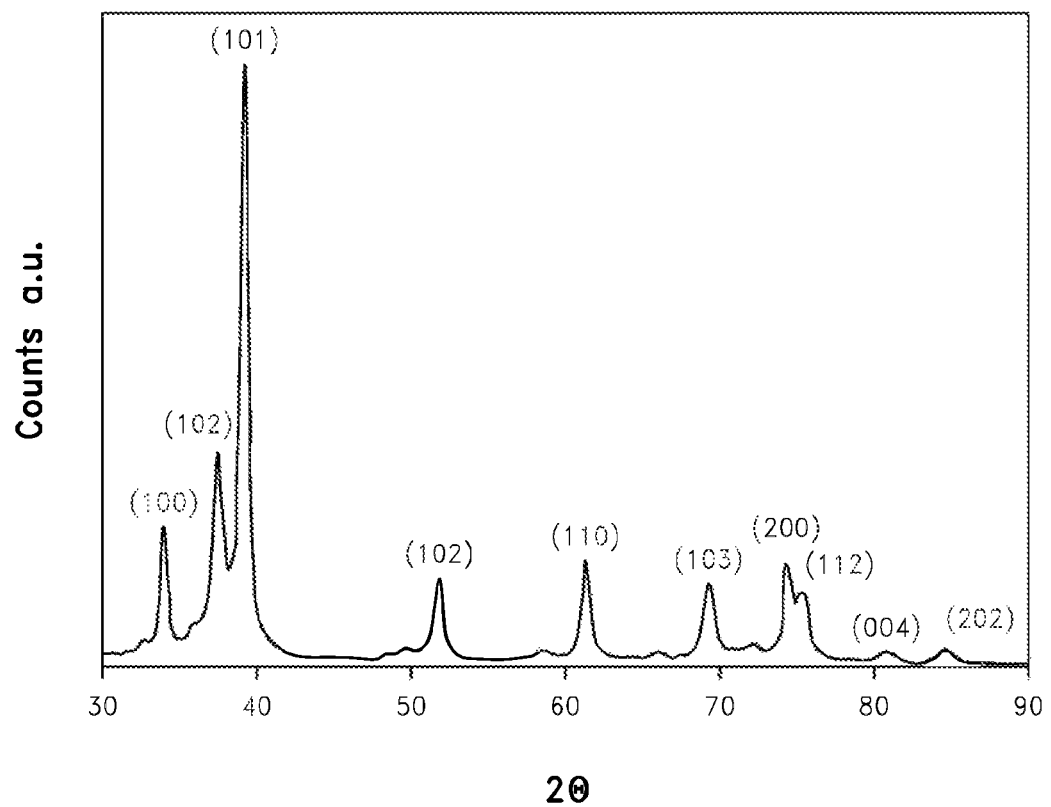
FIG. 1 represents X-ray diffraction pattern of $Mo_2C$ nanoparticles.

One embodiment of the present invention generates the detailed crystal shape information as given above. The crystal shape is very sensitive to the conditions of crystal growth, one and the same crystal structure exhibiting widely different crystal shapes if prepared under different synthetic routes. X-ray diffraction is a versatile tool which is used in the characterization of materials. However, only the crystal structure information (such as the space group and atomic positions) is being presently obtained from XRD and not the external physical shape/habit of crystals which the present invention helps to extract. It is further known that the relative rates of growth along different crystal directions determine the crystal shape. Consequently, embodiments of the present invention will be useful in elucidating how the experimental crystal growth conditions influence the rates of crystal growth in different directions.

The invented algorithm is applied to cubic, tetragonal and hexagonal crystal systems. However, it is not restricted to any particular crystal system. Several interesting crystal shapes can be generated from one and the same crystal system by varying the XRD peak characteristics.

Accordingly, embodiments of the present invention provide a method for computing crystal shapes from X-Ray Diffraction Data (XRD) of a substance, wherein the said method comprises the steps of:

a) obtaining the following input Parameters;
  (i) number of XRD peaks (n)
  (ii) (2θ)-value
  (iii) the peak-width at half maximum (i.e. B value) for each of the XRD peaks b) indexing by assigning the Miller indices (h, k, l) to each of the XRD peaks;

c) obtaining the unit cell parameter by using known methods;

d) using the data gathered from step (a) and step (b) in Scherrer formula ($t_{hkl}=0.9\lambda/B \cos\theta_{hkl}$) to get the crystal thickness in different directions;

e) using the data gathered from steps (a) to (d) and finding the set of crystal planes which determine the mathematical envelope for the crystal shape;

f) finding the co-ordinates of each point of intersection of crystal planes;

g) finding the set of all real points of intersection;

h) identifying a set of real points of intersection which fall on each plane;

i) transforming of coordinates of real points of intersections from Global to Local frames;

j) finding of the polar co-ordinate [$\theta_i$] of each vertex ordered in an ascending series in each crystal face;

k) finding of a transformation T which reshuffles the indices;

l) using the transformation T obtained from step (k), the vertices on each plane are ordered, the areas and Miller indices of each of the exposed crystal faces computed;

m) obtaining the 3D crystal shape as formed by the computer.

One embodiment comprises a computer system having a processor and memory that is configured to receive the data described above and perform the described computation. In one embodiment, the processor and memory are in communication with an X-Ray diffractometer. In one embodiment, the processor and memory are components of the X-Ray diffractometer.

In an embodiment of the present invention, finding the co-ordinates of each point of intersection of crystal planes and the total number of points of intersection, the co-ordinates of each point of intersection and planes which meet at any point of intersection.

Another embodiment of the present invention, finding the following determinants.

$$\Delta = \begin{vmatrix} A_1 & B_1 & C_1 \\ A_2 & B_2 & C_2 \\ A_3 & B_3 & C_3 \end{vmatrix}$$

$$\Delta_x = \begin{vmatrix} -\rho_1 & B_1 & C_1 \\ -\rho_2 & B_2 & C_2 \\ -\rho_3 & B_3 & C_3 \end{vmatrix}$$

$$\Delta_y = \begin{vmatrix} A_1 & -\rho_1 & C_1 \\ A_2 & -\rho_2 & C_2 \\ A_3 & -\rho_3 & C_3 \end{vmatrix}$$

$$\Delta_z = \begin{vmatrix} A_1 & B_1 & -\rho_1 \\ A_2 & B_2 & -\rho_2 \\ A_3 & B_3 & -\rho_3 \end{vmatrix}$$

In yet another embodiment of the present invention, the point of intersection is given by the following equations.

$$x = \frac{\Delta_x}{\Delta}$$

$$y = \frac{\Delta_y}{\Delta}$$

$$z = \frac{\Delta_z}{\Delta}$$

In still another embodiment of the present invention, finding the set of all real points of intersection. If $\rho_i(A_i x + B_i y + C_i z + \rho_i) < -0.0001$ for at least one value of i then the point (x,y,z) is a virtual point of intersection.

In still another embodiment of the present invention, the real points of intersection are computed and the virtual points of intersection are eliminated.

In still another embodiment of the present invention, a set of real points of intersection is identified, which fall on each plane.

In still another embodiment of the present invention, each plane is taken and the real points of intersection falling on it are found using the inequality $(A_i x + B_i y + C_i z + \rho_i)^2 < 0.0001$.

In still another embodiment of the present invention, the real points of intersection are stored plane wise in two dimensional arrays of the form x[p,n1[p]], y[p,n1[p]], z[p,n1[p]], where n1[p] is a one dimensional array which stores the total number of real points of intersection in the $p^{th}$ plane.

In still another embodiment of the present invention, the coordinates of real points of intersection for each plane are computed.

In still another embodiment of the present invention, the coordinates of each of the real points of intersection is expressed in terms of local coordinate system, wherein the local y-axis is normal to the plane in question.

In still another embodiment of the present invention, the local co-ordinates of real points of intersection are computed for each plane.

In still another embodiment of the present invention, the following mathematical procedure is used to express the (3D)-coordinates of the points on a face in terms of the Local reference frame having its origin at the center of the face and its y-axis along the normal to the face.

$$[x_{local} \quad y_{local} \quad z_{local} \quad 1] = \lfloor x_{global} \quad y_{global} \quad z_{global} \quad 1 \rfloor [M^{-1}]$$

$$[M^{-1}] = \begin{bmatrix} a^2 + c^2\cos\phi & c\sin\phi & ac(1-\cos\phi) & 0 \\ -c\sin\phi & \cos\phi & a\sin\phi & 0 \\ ac(1-\cos\phi) & -a\sin\phi & c^2 + a^2\cos\phi & 0 \\ x_0^1 & y_0^1 & z_0^1 & 1 \end{bmatrix}$$

$$a = \frac{-C}{\sqrt{A^2+C^2}}; \; c = \frac{A}{\sqrt{A^2+C^2}}; \; \cos\phi = \frac{B}{\sqrt{A^2+B^2+C^2}}$$

where (A, B, C) is the normal vector to the face.

$$x_0^1 = -x_0(a^2 + c^2\cos\phi) + y_0 c\sin\phi - z_0 ac(1-\cos\phi)$$

$$y_0^1 = -x_0 c\sin\phi - y_0\cos\phi + z_0 a\sin\phi$$

$$z_0^1 = -x_0 ac(1-\cos\phi) - y_0 a\sin\phi - z_0(c^2 + a^2\cos\phi)$$

where ($x_0$, $y_0$, $z_0$) is the center of the face.

In still another embodiment of the present invention, the polar co-ordinate [$\theta_i$] of each vertex is found in each crystal face with respect to the local co-ordinate frame with the y-axis perpendicular to the crystal face.

In still another embodiment of the present invention, a transformation T is found which reshuffles the indices of vertices in each plane to corresponds the new ordering to the polar angles in an ascending order.

In still another embodiment of the present invention, the vertices on each plane are ordered by using the transformation T and the area and Miller indices of each of the exposed crystal faces are found. The area calculation proceeds as follows.

$$s1 = \sqrt{[xc(p) - xpl(p,i)]^2 + [zc(p) - zpl(p,i)]^2}$$

$$s2 = \sqrt{[xc(p) - xpl(p,i+1)]^2 + [zc(p) - zpl(p,i+1)]^2}$$

$$s3 = \sqrt{[xpl(p,i+1) - xpl(p,i)]^2 + [zpl(p,i+1) - zpl(p,i)]^2}$$

$$s = (s1 + s2 + s3)/2$$

$$area = \sqrt{s*(s-s1)*(s-s2)*(s+s3)}$$

xc=The x co-ordinate center zc=The z co-ordinate center

In still another embodiment of the present invention, the crystal faces of the crystal are computed as a set of polygons in 3D by using the ordered set of vertices of each polygonal face.

In still another embodiment of the present invention, the x-ray diffractometer is used to generate the external shape of crystals.

In still another embodiment of the present invention, the said method is useful for finding the crystal shapes from arbitrary angles.

In still another embodiment of the present invention, the said method is useful for finding the crystal shapes of nano crystal and materials

TABLE 1

Bravais Lattices, Crystal Systems and Unit Cell Dimensions

| System | Unit Cell Dimensions | Bravais lattices |
|---|---|---|
| Cubic (Isometric) | a = b = c | Simple |
| | α = β = γ = 90° | Body-centered |
| | | Face-centered |
| Tetragonal | a = b ≠ c | Simple |
| | α = β = γ = 90° | Body-centered |
| Orthorhombic | a ≠ b ≠ c | Simple |
| | α = β = γ = 90° | Body-centered |
| | | Face-centered |
| | | End-centered |
| Monoclinic | a ≠ b ≠ c | Simple |
| | α = γ = 90° ≠ β | End-centered |
| Triclinic | a ≠ b ≠ c | Simple |
| | α ≠ β ≠ γ | |
| Hexagonal | a = b ≠ c | Simple |
| | α = β = 90° | |
| | γ = 120° | |
| Rhombohedral | a = b = c | Simple |
| | α = β = γ ≠ 90° | |

Figure 4:
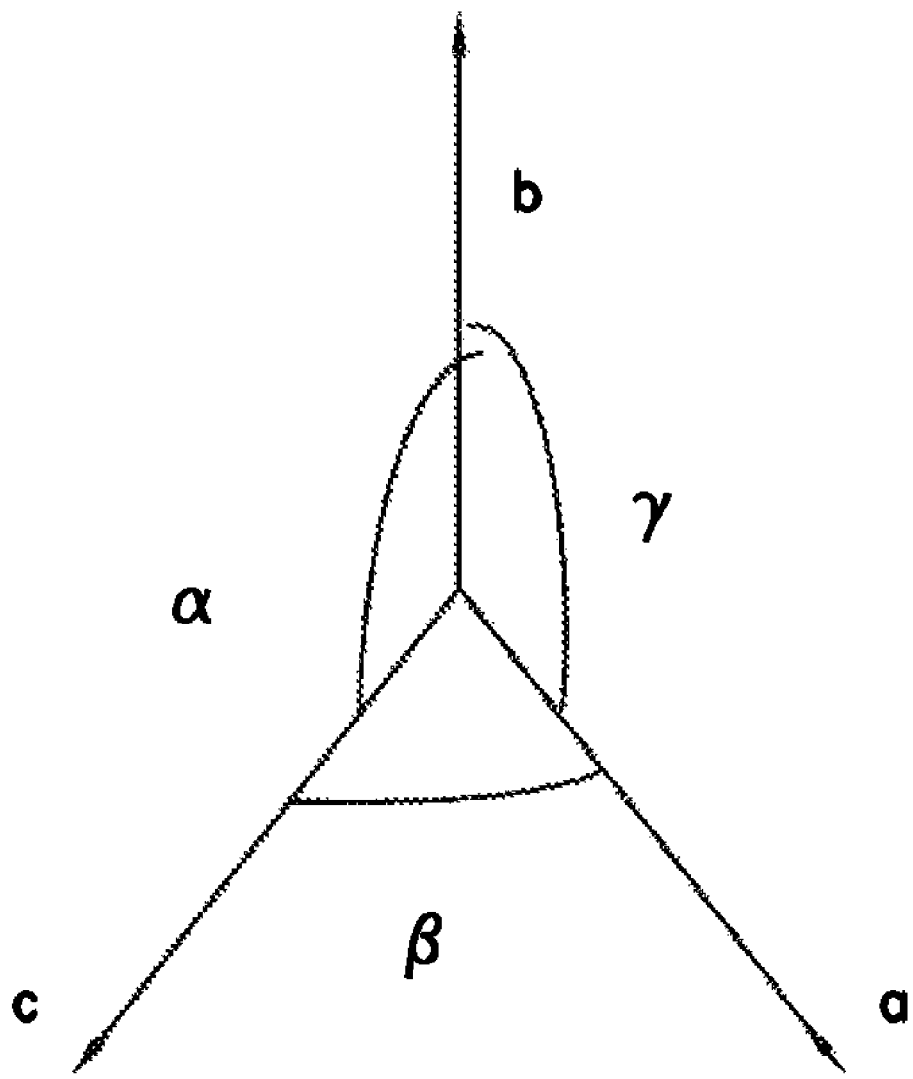
FIG. 4 illustrates an example of vectors representing crystal axes.

In FIG. 4, the vectors $\vec{a}$, $\vec{b}$, $\vec{c}$ represent the crystal axes, α is the angle subtended between axes b and c, β that between a and c, and γ that between a and b.

| Name | Description |
|---|---|
| $A_i, B_i, C_i, \rho_i$ | Parameters characterizing the $i^{th}$ plane |
| $x_{global}, y_{global}, z_{global}$ | The co-ordinates of any given vertex in the global frame. |
| $x_{local}, y_{local}, z_{local}$ | The co-ordinates of any given vertex in the local frame |
| $\theta_i$ | The polar coordinates of vertices |
| T | The transformation which orders the vertex indices corresponding to increasing polar angles in each polygonal face. |
| xc(p), zc(p) | The x and z co-ordinates of the center of the $p^{th}$ polygonal face in the local co-ordinate frame |
| xpl(p, i), zpl(p, i) | The x and z co-ordinates of the $i^{th}$ T-ordered vertex in the $p^{th}$ face in the local coordinate frame |

The following examples are given the way of illustration and should not construed to limit the scope of the present invention.

EXAMPLE 1

Crystal Shape of Mo$_2$C Computed from the XRD Data in FIG. 1

| Inputs to the crystal shape algorithm | Outputs from crystal shape algorithm | |
|---|---|---|
| 1) Number of XRD peaks (n) 8 | 1) Miller indices of the crystal faces exposed [0 0 2], [0 0 2], [1 0 1], [1 0 1], [1 1 0], [1 1 0], [1 0 3], [1 0 3], [2 0 0], [200], [1 1 2], [1 1 2] | |
| 2) The values of 2θ in degrees for each peak | 2) Areas of the crystal faces: | |
| | Crystal face exposed | Area (Å)$^2$ |
| 34.1096, 37.80824, | 0 0 2 | 3310.258433 |
| 39.45208, 52.19184, | 0 0 2 | 3310.258433 |
| 61.64382, 69.45216, | 1 0 1 | 1778.180670 |
| 74.38368, 75.61656 | 1 0 1 | 1778.180670 |

Figure 5:
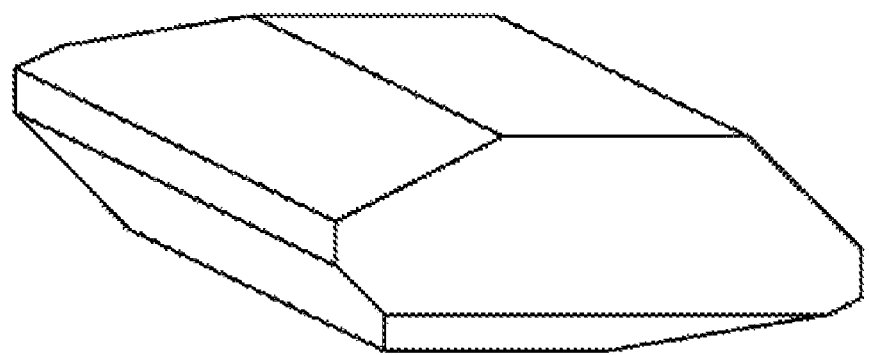
FIG. 5 illustrates an example of a crystal shape of $Mo_2C$ computed from the XRD data in FIG. 1.

| Inputs to the crystal shape algorithm | Outputs from crystal shape algorithm | |
|---|---|---|
| -continued | | |
| | 1 1 0 | 2652.302839 |
| | 1 1 0 | 2652.302839 |
| | 1 0 3 | 10203.70015 |
| | 1 0 3 | 8356.776426 |
| | 2 0 0 | 5471.938196 |
| | 2 0 0 | 7192.017308 |
| | 1 1 2 | 19469.01519 |
| | 1 1 2 | 18736.15285 |
| 3) The values of B in radians for each peak 0.01076, 0.01435, 0.01435, 0.01435, 0.01435, 0.02153, 0.01435, 0.02511 | 3) Crystal shape generated is illustrated in FIG. 5. | |
| 4) The Miller indices of XRD peaks [h, k, l] [1 0 0], [0 0 2], [1 0 1], [1 0 2], [1 1 0], [1 0 3], [2 0 0], [1 1 2] | | |
| 5) Unit Cell Parameters (a, b, c, α, β, γ) a = b = 3.0124Å, c = 4.735Å α = β = γ = 90° | | |

This corresponds to the XRD data of Mo$_2$C which exhibits 8 peaks and belongs to tetragonal system. The crystal shape algorithm has computed 12 exposed faces for this crystal. It is to be noted that some pairs of opposite faces have equal areas while others have unequal areas. The actual crystal shape found is also shown.

EXAMPLE 2

Figure 2:
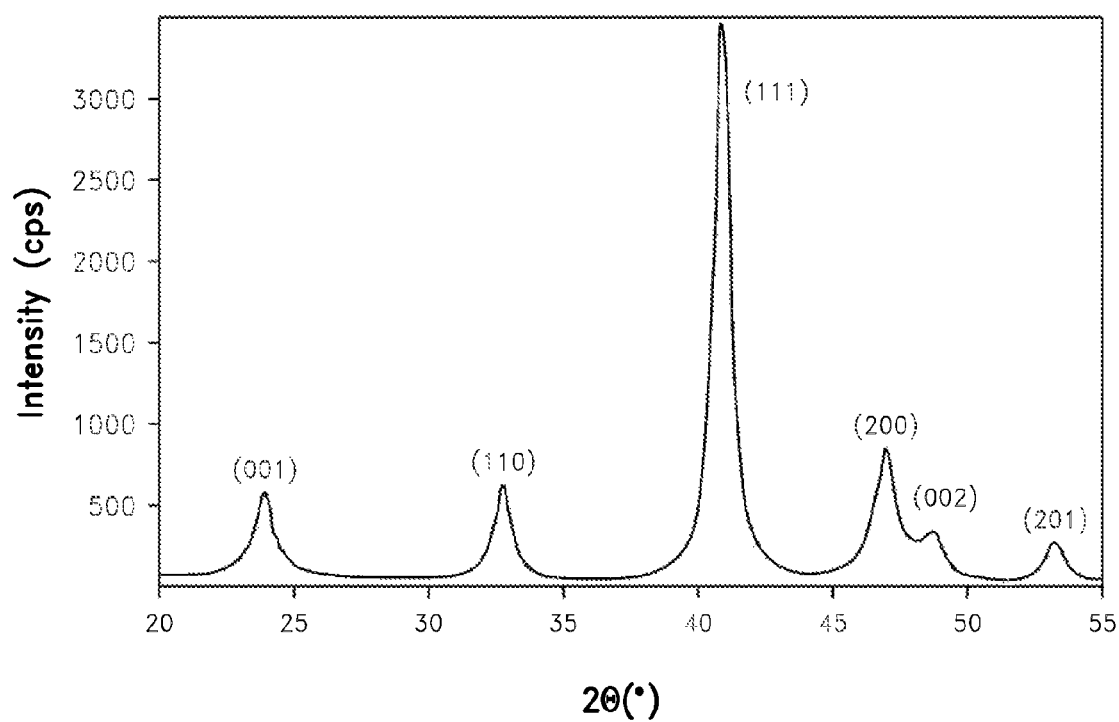
FIG. 2 represents X-ray diffraction pattern of FePt nanoparticles.
Figure 3:
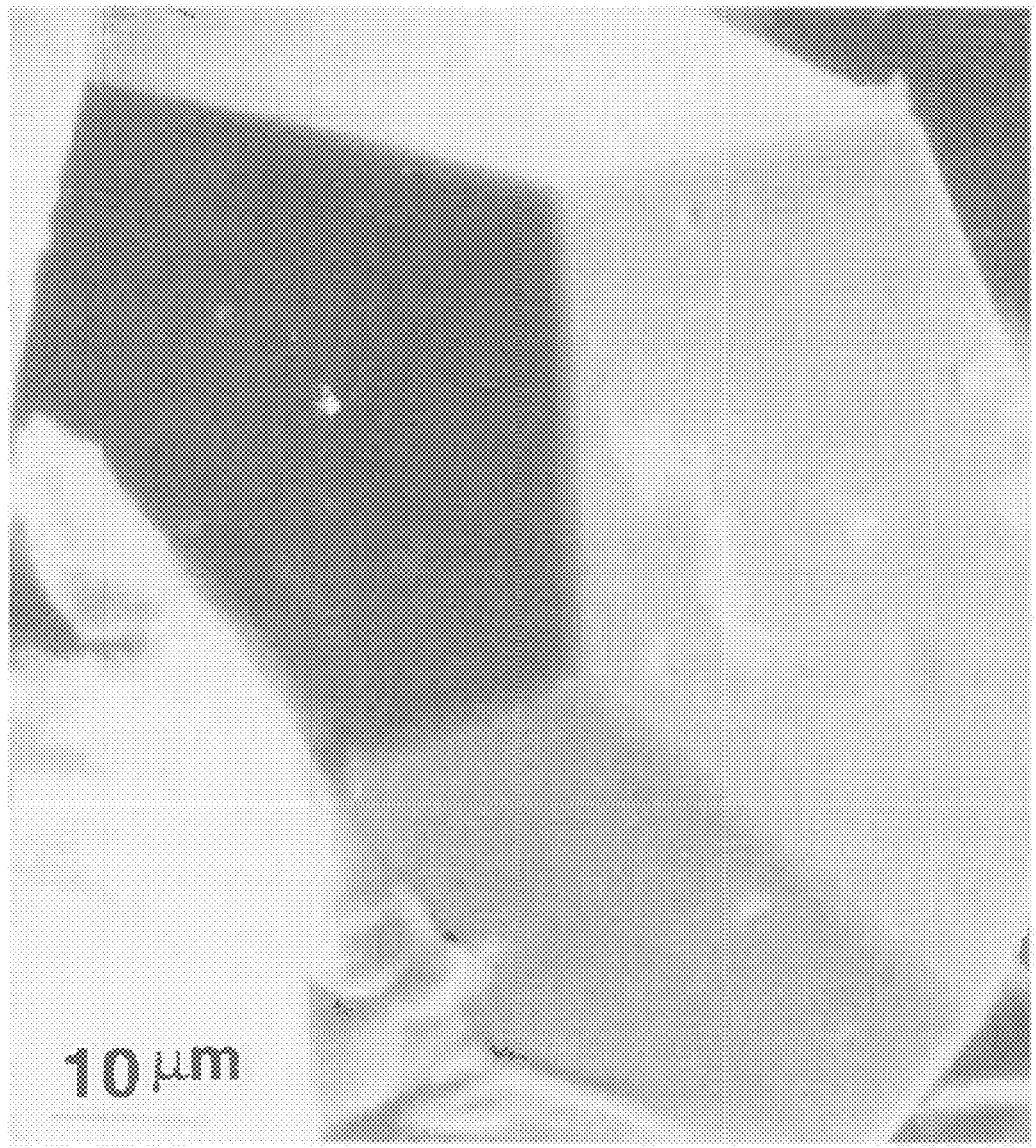
FIG. 3 represents SEM photograph of a quasicrystal of a 63% Al, 25% Cu-11% Fe alloy showing pentagonal dodecahedral faces.

Crystal Shape of FePt Computed from the XRD Data in FIG. 2

Figure 6:
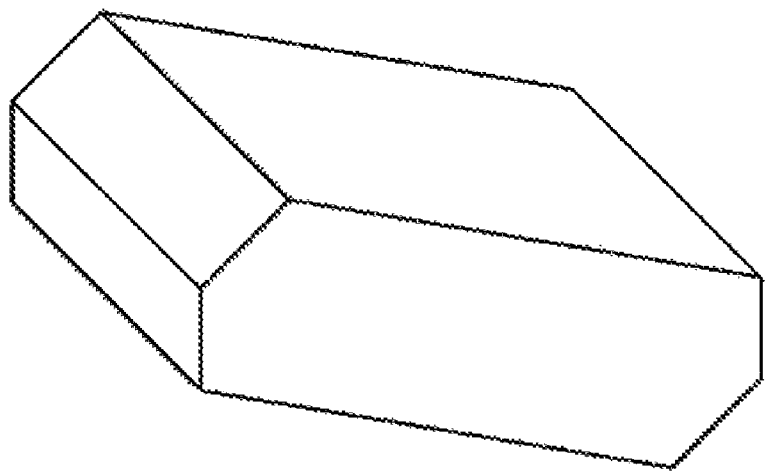
FIG. 6 illustrates an example of a crystal shape of FePt computed from the XRD data in FIG. 2.

| Inputs to the crystal shape algorithm | Outputs from crystal shape algorithm | |
|---|---|---|
| 1) Number of XRD peaks (n) 6 | 1) Miller indices of the crystal faces exposed [1 1 0], [1 1 0], [2 0 0], [200],[0 0 2], [0 0 2], [2 0 1], [2 0 1] | |
| 2) The values of 2θ in degrees for each peak | Areas of the crystal faces: | |
| | Crystal face exposed | Area(Å)$^2$ |
| 23.9, 32.75, 40.7, 47.3, 48.8, 53.45 | 110 | 5420.241924 |
| | 110 | 5420.241924 |
| 3) The values of B in radians for each peak | 200 | 1785.43609 |
| | 200 | 1785.43609 |
| 0.02095, 0.01571, 0.0131, | 002 | 5140.74441 |
| 0.01571, 0.02619, 0.01833 | 002 | 5140.74441 |
| 4) The Miller indices of XRD peaks [h, k, l] [0 0 1], [1 1 0], [1 1 1], [2 0 0], [0 0 2], [2 0 1] | 201 | 2152.27397 |
| | 201 | 2152.27397 |
| 5) Unit Cell Parameters (a, b, c, α, β, γ) a = b = 3.838Å, c = 3.715Å α = β = γ = 90° | 3) Crystal shape generated is illustrated in FIG. 6. | |

This corresponds to the XRD data of Fe—Pt which exhibits 6 peaks and belongs to tetragonal system. The crystal shape algorithm has computed 8 exposed faces for this crystal. It is to be noted that each pair of opposite faces have equal areas. The actual crystal shape found is also shown.

EXAMPLE 3

Crystal Shape of VN Computed from the XRD Data

Figure 7:
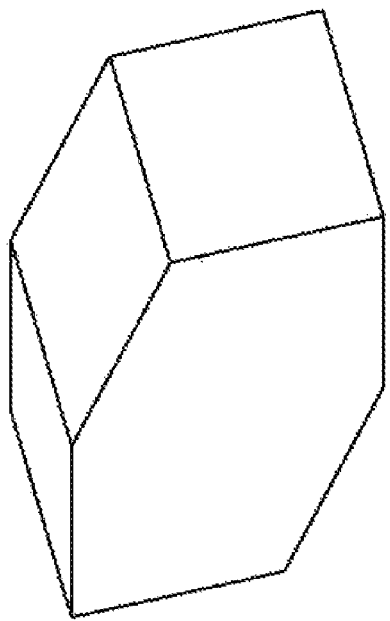
FIG. 7 illustrates an example of a crystal shape of VN computed from the XRD data.

| Inputs to the crystal shape algorithm | Outputs from crystal shape algorithm | |
|---|---|---|
| 1) Number of XRD peaks (n) 5 | 1) Miller indices of the crystal faces exposed [2 0 0], [2 0 0], [2 2 0], [2 2 0], [3 3 1], [3 3 1], [2 2 2], [2 2 2] | |
| 2) The values of 2θ in degrees for each peak | Areas of the crystal faces : | |
| | Crystal face exposed | Area(Å)$^2$ |
| 37.6446, 43.595, 63.6775, 76.3222, 80.4131 | 2 0 0 | 8150.96617 |
| | 2 0 0 | 8150.96617 |
| 3) The values of B in radians for each peak | 2 2 0 | 27050.93651 |
| | 2 2 0 | 27050.93651 |
| 0.00649, 0.00974, 0.01299, | 3 3 1 | 14440.18875 |
| 0.01948, 0.01623 | 3 3 1 | 14440.18875 |
| 4) The Miller indices of XRD peaks [h, k, l] [1 1 1], [2 0 0], [2 2 0], [3 1 1], [2 2 2] | 2 2 2 | 15567.00054 |
| | 2 2 2 | 15567.00054 |
| 5) Unit Cell Parameters (a, b, c, α, β, γ) a = b = c = 4.133Å, α = β = γ = 90° | 3) Crystal shape generated is illustrated in FIG. 7. | |

This corresponds to the XRD data of VN which exhibits 5 peaks and belongs to cubic system. The crystal shape algorithm has computed 8 exposed faces for this crystal. It is to be noted that each pair of opposite faces have equal areas. The actual crystal shape found is also shown. The XRD and TEM of VN are reported in Materials Research Bulletin 39, 957, 2004.

EXAMPLE 4

Crystal Shape Computed from Hypothetical Data

Figure 8:
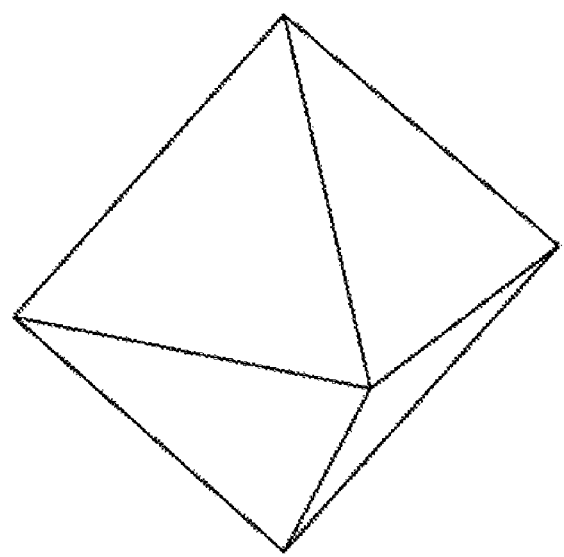
FIG. 8 illustrates an example of a crystal shape computed from hypothetical data.
Figure 9:
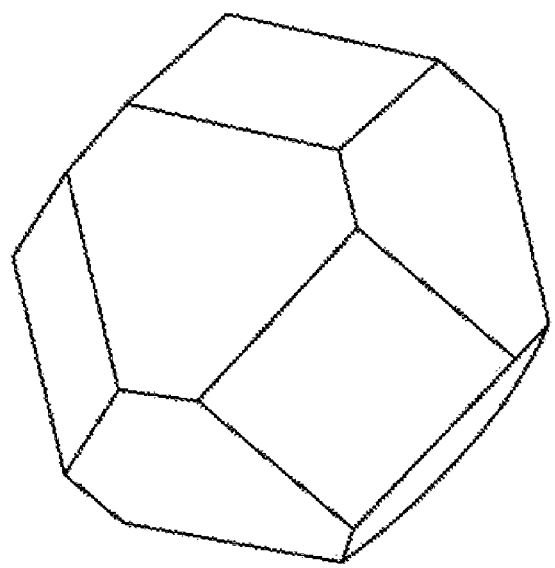
FIG. 9 illustrates another example of a crystal shape computed from hypothetical data.

| Inputs to the crystal shape algorithm | Outputs from crystal shape algorithm | |
|---|---|---|
| 1) Number of XRD peaks (n) 7 | 1) Miller indices of the crystal faces exposed [1 1 1], [1 1 1], [−1 1 1], [−1 1 1], [−1 1 −1], [−1 1 −1], [1 1 −1], [1 1 −1] | |
| 2) The values of 2θ in degrees for each peak | Areas of the crystal faces: | |
| | Crystal face exposed | Area(Å)$^2$ |
| 8.83574, 17.7234, 26.72132, 15.33338, 30.95026, 47.18512, 64.5048 | 1 1 1 | 238.15698 |
| | 1 1 1 | 238.15698 |
| | −1 1 1 | 216.50635 |
| 3) The values of B in radians for each peak | −1 1 1 | 216.50635 |
| | −1 1 −1 | 151.55444 |
| 0.00335, 0.00338, 0.00344, 0.13834, 0.14226, 0.14961, 0.16212 | −1 1 −1 | 151.55444 |
| | 1 1 −1 | 173.20508 |
| 4) The Miller indices of XRD peaks [h, k, l] [1 0 0], [0 1 0], [0 0 1], [1 1 1], [−1 1 1], [−1 1 −1], [1 1 −1] | 1 1 −1 | 173.20508 |
| 5) Unit Cell Parameters (a, b, c, α, β, γ) a = b = c = 10 Å, α = β = γ = 90° | 3) Crystal shape generated is illustrated in FIG. 8. | |

Examples 4 to 9 show 6 different crystal shapes for a crystal structure having the same unit cell parameters. They all have their XRD peaks at the same 2θ-positions and differ only in the peak-widths at half maximum. It is interesting to note that a host of different crystal shapes are possible just by varying the peak widths. This is akin to the growth of NaCl crystals in varying concentrations of urea which influence the crystal shape [A. R. Verma, O. N. Srivastava Crystallography applied to solid state physics, Second Edition, New Age International, New Delhi, 2001]

EXAMPLE 5

Crystal Shape Computed from Hypothetical Data

| Inputs to the crystal shape algorithm | Outputs from crystal shape algorithm | |
|---|---|---|
| 1) Number of XRD peaks (n) 7 | 1) Miller indices of the crystal faces exposed [1 0 0], [1 0 0], [0 1 0], [0 1 0], [0 0 1], [0 0 1], [1 1 1], [1 1 1], [−1 1 1], [−1 1 1], [−1 1 −1], [−1 1 −1], [1 1 −1], [1 1 −1] | |
| 2) The values of 2θ in degrees for | Areas of the crystal faces: | |
| each peak | Crystal face exposed | Area(Å)² |
| 8.83574, 17.7234, 26.72132, | 1 0 0 | 13.39809 |
| 15.33338, 30.95026, 47.18512, | 1 0 0 | 13.39809 |
| 64.5048, | 0 1 0 | 13.39809 |
| 3) The values of B in radians for each | 0 1 0 | 13.39809 |
| peak | 0 0 1 | 13.39809 |
| 0.13751, 0.13876, 0.14092, 0.13834, | 0 0 1 | 13.39809 |
| 0.14226, 0.14961, 0.16212 | 1 1 1 | 35.04809 |
| 4) The Miller indices of XRD peaks | 1 1 1 | 35.04809 |
| [h, k, l] | −1 1 1 | 35.04809 |
| [1 0 0], [0 1 0], [0 0 1], [1 1 1], | −1 1 1 | 35.04809 |
| [−1 1 1], [−1 1 −1], [1 1 −1] | −1 1 −1 | 35.04809 |
| | −1 1 −1 | 35.04809 |
| | 1 1 −1 | 35.04809 |
| | 1 1 −1 | 35.04809 |
| 5) Unit Cell Parameters (a, b, c, α, β, γ) a = b = c = 10 Å, α = β = γ = 90° | 3) Crystal shape generated is illustrated in FIG. 8. | |

EXAMPLE 6

Crystal Shape Computed from Hypothetical Data

Figure 10:
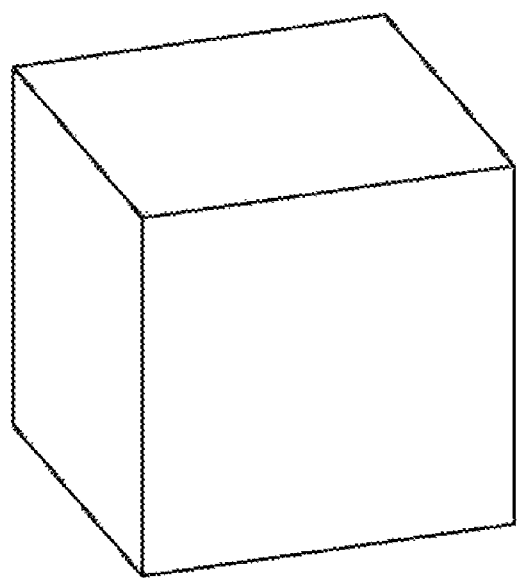
FIG. 10 illustrates still another example of a crystal shape computed from hypothetical data.

| Inputs to the crystal shape algorithm | Outputs from crystal shape algorithm | |
|---|---|---|
| 1) Number of XRD peaks (n) 7 | 1) Miller indices of the crystal faces exposed [1 0 0], [1 0 0], [0 1 0], [0 1 0], [0 0 1], [0 0 1] | |
| 2) The values of 2θ in degrees for | Areas of the crystal faces: | |
| each peak | Crystal face exposed | Area(Å)² |
| 8.83574, 17.7234, 26.72132, | 1 0 0 | 50.0 |
| 15.33338, 30.95026, 47.18512, | 1 0 0 | 50.0 |
| 64.5048 | 0 1 0 | 50.0 |
| 3) The values of B in radians for each | 0 1 0 | 50.0 |
| peak | 0 0 1 | 50.0 |
| 0.13751, 0.13876, 0.14092, 0.01383, | 0 0 1 | 50.0 |
| 0.01423, 0.01496, 0.01621 | | |
| 4) The Miller indices of XRD peaks | | |
| [h, k, l] | | |
| [1 0 0], [0 1 0], [0 0 1], [1 1 1], | | |
| [−1 1 1], [−1 1 −1], [1 1 −1] | | |
| 5) Unit Cell Parameters (a, b, c, α, β, γ) a = b = c = 10 Å, α = β = γ = 90° | 3) Crystal shape generated is illustrated in FIG. 10. | |

EXAMPLE 7

Crystal Shape Computed from Hypothetical Data

Figure 11:
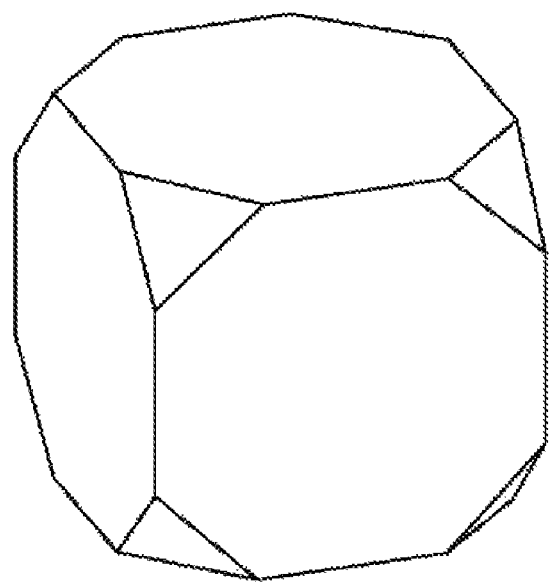
FIG. 11 illustrates still another example of a crystal shape computed from hypothetical data.

| Inputs to the crystal shape algorithm | Outputs from crystal shape algorithm | |
|---|---|---|
| 1) Number of XRD peaks (n) 7 | 1) Miller indices of the crystal faces exposed [1 0 0], [1 0 0], [0 1 0], [0 1 0], [0 0 1], [0 0 1], [1 1 1], [1 1 1], [−1 1 1], [−1 1 1], [−1 1 −1], [−1 1 −1], [1 1 −1], [1 1 −1] | |
| 2) The values of 2θ in degrees for | Areas of the crystal faces: | |
| each peak | Crystal face exposed | Area(Å)² |
| 8.83574, 17.7234, 26.72132, | 1 0 0 | 4987.17782 |
| 15.33338, 30.95026, 47.18512, | 1 0 0 | 4987.17782 |
| 64.5048 | 0 1 0 | 4130.47866 |
| 3) The values of B in radians for each | 0 1 0 | 4130.47866 |
| peak | 0 0 1 | 3273.7795 |
| 0.01964, 0.01982, 0.020131, | 0 0 1 | 3273.7795 |
| 0.01383, 0.01423, 0.01496, | 1 1 1 | 293.12060 |
| 0.01621 | 1 1 1 | 293.12060 |
| 4) The Miller indices of XRD peaks | −1 1 1 | 293.12060 |
| [h, k, l] | −1 1 1 | 293.12060 |
| [1 0 0], [0 1 0], [0 0 1], [1 1 1], | −1 1 −1 | 293.12060 |
| [−1 1 1], [−1 1 −1], [1 1 −1] | −1 1 −1 | 293.12060 |
| | 1 1 −1 | 293.12060 |
| | 1 1 −1 | 293.12060 |
| 5) Unit Cell Parameters (a, b, c, α, β, γ) a = b = c = 10 Å, α = β = γ = 90° | 3) Crystal shape generated is illustrated in FIG. 11. | |

EXAMPLE 8

Crystal Shape Computed from Hypothetical Data

| Inputs to the crystal shape algorithm | Outputs from crystal shape algorithm | |
|---|---|---|
| 1) Number of XRD peaks (n) 7 | 1) Miller indices of the crystal faces exposed [1 0 0], [1 0 0], [0 1 0], [0 1 0], [0 0 1], [0 0 1], [1 1 1], [1 1 1], [−1 1 1], [−1 1 1], [−1 1 −1], [−1 1 −1], [1 1 −1], [1 1 −1] | |
| 2) The values of 2θ in degrees for | Areas of the crystal faces: | |
| each peak | Crystal face exposed | Area(Å)² |
| 8.83574, 17.7234, 26.72132, | 1 0 0 | 1529.00866 |
| 15.33338, 30.95026, 47.18512, | 1 0 0 | 1529.00866 |
| 64.5048 | 0 1 0 | 1529.04324 |
| 3) The values of B in radians for each | 0 1 0 | 1529.04324 |
| peak | 0 0 1 | 1529.04324 |
| 0.01448, 0.01461, 0.01483, | 0 0 1 | 1529.04324 |
| 0.01383, 0.01423, 0.014961, | 1 1 1 | 3215.90316 |
| 0.01621 | 1 1 1 | 3215.90316 |

-continued

Figure 12:
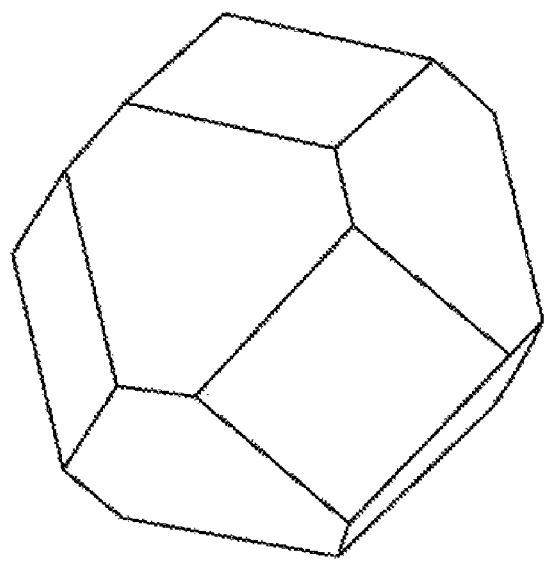
FIG. 12 illustrates still another example of a crystal shape computed from hypothetical data.

| Inputs to the crystal shape algorithm | Outputs from crystal shape algorithm | |
|---|---|---|
| 4) The Miller indices of XRD peaks [h, k, l] [1 0 0], [0 1 0], [0 0 1], [1 1 1], [−1 1 1], [−1 1 −1], [1 1 −1] | −1 1 1 | 3426.99686 |
| | −1 1 1 | 3426.99686 |
| | −1 1 −1 | 3215.90316 |
| | −1 1 −1 | 3215.90316 |
| | 1 1 −1 | 3426.99686 |
| | 1 1 −1 | 3426.99686 |
| 5) Unit Cell Parameters (a, b, c, α, β, γ) a = b = c = 10 Å, α = β = γ = 90° | 3) Crystal shape generated is illustrated in FIG. 12. | |

EXAMPLE 9

Crystal Shape Computed from Hypothetical Data

Figure 13:
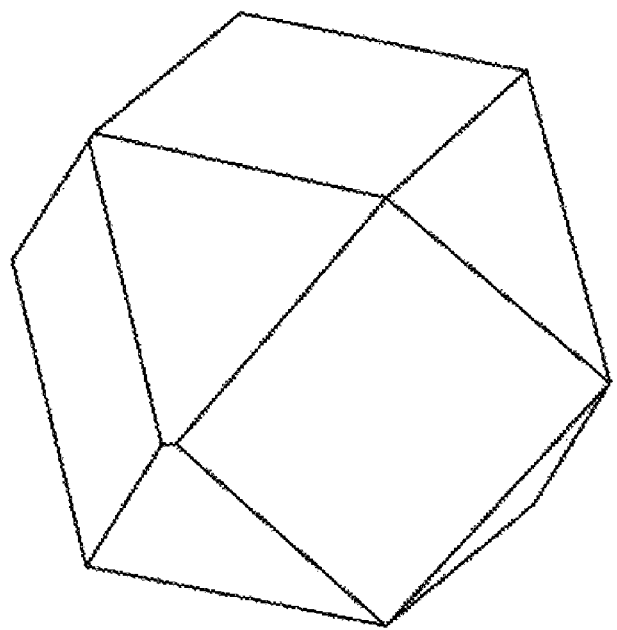
FIG. 13 illustrates still another example of a crystal shape computed from hypothetical data.

| Inputs to the crystal shape algorithm | Outputs from crystal shape algorithm | |
|---|---|---|
| 1) Number of XRD peaks (n) 7 | 1) Miller indices of the crystal faces exposed [1 0 0], [1 0 0], [0 1 0], [0 1 0], [0 0 1], [0 0 1], [1 1 1], [1 1 1], [−1 1 1], [−1 1 1], [−1 1 −1], [−1 1 −1], [1 1 −1], [1 1 −1] | |
| 2) The values of 2θ in degrees for each peak | Areas of the crystal faces: | |
| | Crystal face exposed | Area(Å)² |
| 8.83574, 17.7234, 26.72132, 15.33338, 30.95026, 47.18512, 64.5048 | 1 0 0 | 1814.97645 |
| | 1 0 0 | 1814.97645 |
| | 0 1 0 | 1815.01577 |
| 3) The values of B in radians for each peak | 0 1 0 | 1815.01577 |
| | 0 0 1 | 1815.01577 |
| 0.01563, 0.01577, 0.01601, 0.01383, 0.01423, 0.01496, 0.01621 | 0 0 1 | 1815.01577 |
| | 1 1 1 | 2793.24779 |
| | 1 1 1 | 2793.24779 |
| 4) The Miller indices of XRD peaks [h, k, l] [1 0 0], [0 1 0], [0 0 1], [1 1 1], [−1 1 1], [−1 1 −1], [1 1 −1] | −1 1 1 | 3281.68612 |
| | −1 1 1 | 3281.68612 |
| | −1 1 −1 | 2793.24779 |
| | −1 1 −1 | 2793.24779 |
| | 1 1 −1 | 3281.68612 |
| | 1 1 −1 | 3281.68612 |
| 5) Unit Cell Parameters (a, b, c, α, β, γ) a = b = c = 10 Å, α = β = γ = 90° | 3) Crystal shape generated is illustrated in FIG. 13. | |

EXAMPLE 10

Crystal Shape Computed from XRD of CeO₂

| Inputs to the crystal shape algorithm | Outputs from crystal shape algorithm | |
|---|---|---|
| 1) Number of XRD peaks (n) 4 | 1) Miller indices of the crystal faces exposed [1 1 1], [1 1 1], [2 0 0], [2 0 0], [2 2 0], [2 2 0], [3 1 1], [3 1 1]. | |
| 2) The values of 2θ in degrees for each peak | Areas of the crystal faces: | |
| | Crystal face exposed | Area(Å)² |
| 28.49, 33.05, 47.45, 56.18 | 1 1 1 | 4688.620595 |
| 3) The values of B in radians for each peak | 1 1 1 | 4688.620595 |
| | 2 0 0 | 8305.683623 |

Figure 14:
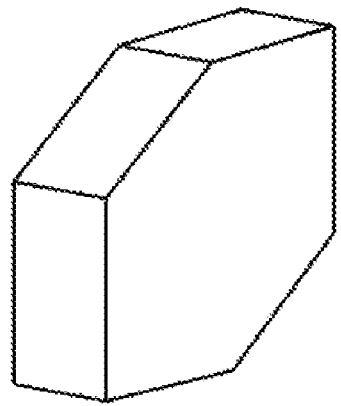
FIG. 14 illustrates an example of a crystal shape computed from XRD data of $CeO_2$.
Figure 15:
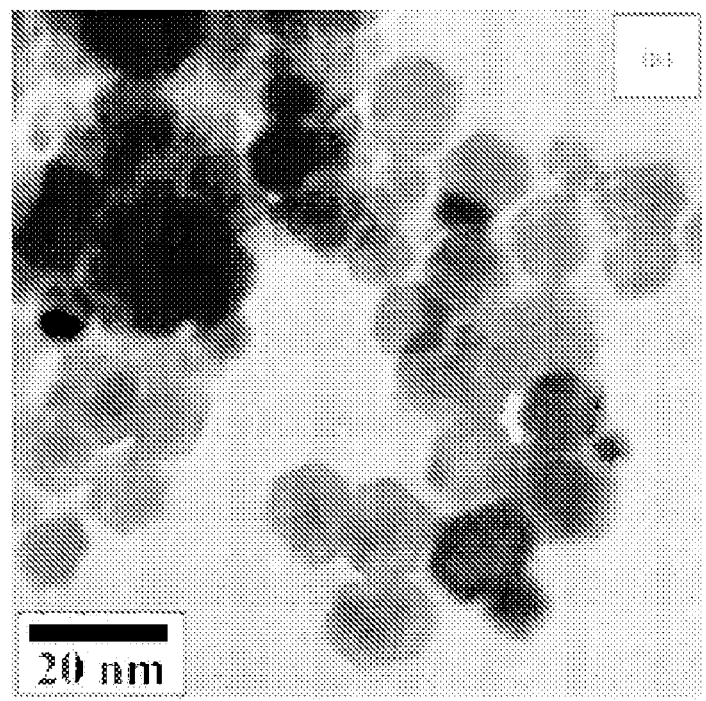
FIG. 15 illustrates an example of a crystal shape experimentally found using TEM.

| Inputs to the crystal shape algorithm | Outputs from crystal shape algorithm | |
|---|---|---|
| 0.010381, 0.01557, 0.0181681, 0.020763 | 2 0 0 | 8305.683623 |
| | 2 2 0 | 19819.95143 |
| 4) The Miller indices of XRD peaks [h, k, l] [1 1 1], [2 0 0], [2 2 0], [3 1 1] | 2 2 0 | 19819.95143 |
| | 3 1 1 | 7856.832086 |
| | 3 1 1 | 7856.832086 |
| 5) Unit Cell Parameters (a, b, c, α, β, γ) a = b = c = 5.415 Å, α = β = γ = 90° | 3) Crystal shape generated is illustrated in FIG. 14. | |

This corresponds to the XRD data of CeO₂ which exhibits 4 peaks and belongs to cubic system. The crystal shape algorithm has computed 8 exposed faces for this crystal. It is to be noted that each pair of opposite faces have equal areas. The actual crystal shape found is also shown. The XRD and TEM of CeO₂ are reported in Colloids and Surfaces A: Physicochemical and Engineering Aspects, 242, 61, 2004.

Figure 16:
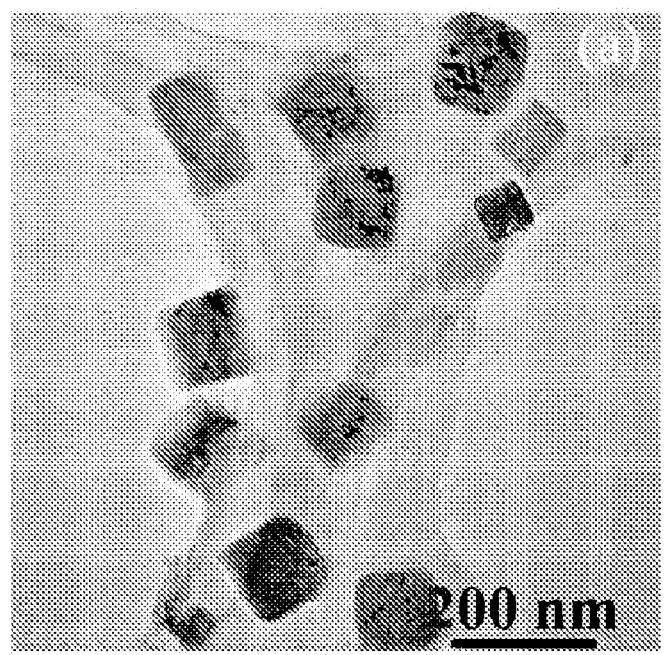
FIG. 16 illustrates a crystal shape of the germanium crystal experimentally found using TEM.

FIG. 16 shows the crystal shape as experimentally found using the transmission electron microscope (TEM). The linear dimension of the crystal is reported to be 15 nm and the shape is hexagonal. The present mathematical algorithm results in a linear dimension of 14.07 nm and generates a hexagonal crystal shape which agrees well with the TEM photograph.

EXAMPLE 11

Crystal Shape Computed from XRD of Germanium Crystal

Figure 17:
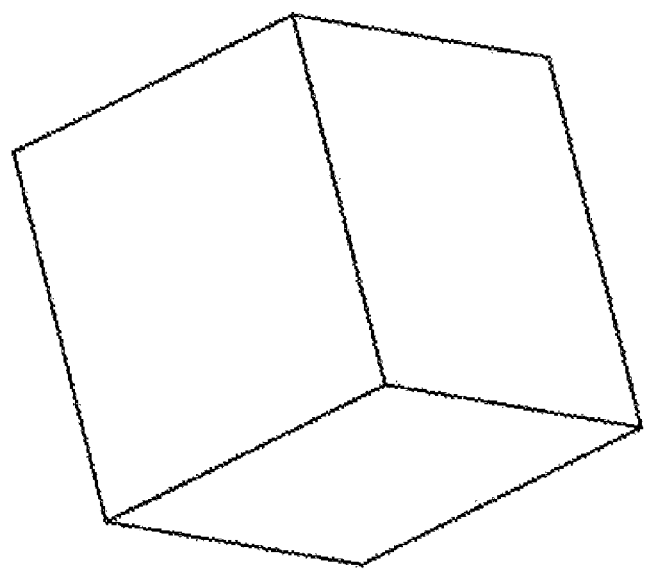
FIG. 17 illustrates an example of crystal shape computed from XRD data of germanium crystal.

| Inputs to the crystal shape algorithm | Outputs from crystal shape algorithm | |
|---|---|---|
| 1) Number of XRD peaks (n) 4 | 1) Miller indices of the crystal faces exposed [1 1 1], [1 1 1], [2 2 0], [2 2 0], [4 2 2], [4 2 2] | |
| 2) The values of 2θ in degrees for each peak | Areas of the crystal faces: | |
| | Crystal face exposed | Area(Å)² |
| 27.82828281, 45.68181817, 54.34343436, 84.04040404 | 1 1 1 | 72240.16128 |
| | 1 1 1 | 72240.16128 |
| 3) The values of B in radians for each peak | 2 2 0 | 45729.95587 |
| | 2 2 0 | 45729.95587 |
| 0.009255533913, 0.006170355941, 0.006170355941, 0.01851106783 | 4 2 2 | 110580.1088 |
| | 4 2 2 | 110580.1088 |
| 4) The Miller indices of XRD peaks [h, k, l] [1 1 1], [2 2 0], [3 3 1], [4 2 2], 5) Unit Cell Parameters (a, b, c, α, β, γ) a = b = c = 5.655 Å, α = β = γ = 90° | 3) Crystal shape generated is illustrated in FIG. 17. | |

This corresponds to the XRD data of Germanium nanocrystals which belongs to the cubic system. The crystal shape algorithm has computed 6 exposed faces for this crystal. It is to be noted that each pair of opposite faces have equal areas. The crystal shape generated by this algorithm is also shown. The XRD and TEM of Ge are reported in Langmuir 21, 751, 2005

FIG. 16 shows the crystal shape as experimentally found using the transmission electron microscope (TEM). The present mathematical algorithm generates a cubic crystal shape which agrees well with the TEM photograph. It is further interesting to note that, near the top left corner of the TEM, two nano-cubes are joined to give a rectangular appearance. The authors also mention that these cubic nanocrystals were synthesized using the surfactant $C_{12}E_7$ as a shape-controlling agent.

EXAMPLE 12

Crystal Shape Computed from XRD of $In_2O_3$ Crystal

Figure 18:
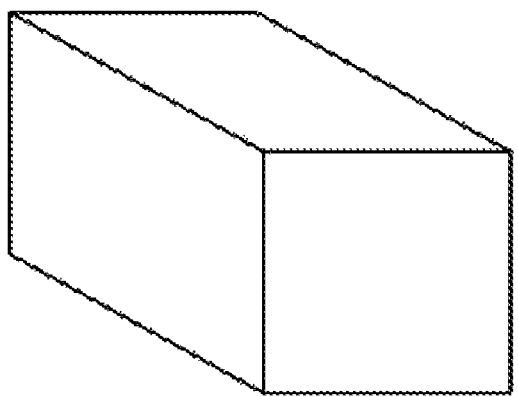
FIG. 18 illustrates a crystal shape computed from XRD data of $In_2O_3$ crystal.

| Inputs to the crystal shape algorithm | Outputs from crystal shape algorithm | | |
|---|---|---|---|
| 1) Number of XRD peaks (n) 7 | 1) Miller indices of the crystal faces exposed [2 2 2], [2 2 2], [4 0 0], [4 0 0], [4 4 0], [4 4 0] | | |
| 2) The values of 2θ in degrees for | Areas of the crystal faces: | | |
| each peak | Crystal face exposed | | Area(Å)$^2$ |
| 21.47385359, 30.40909108, 35.29123110, 36.67296886, 41.73934065, 45.51609048, 50.85880981 | 2 2 2<br>2 2 2<br>4 0 0<br>4 0 0 | | 172511.3577<br>172511.3577<br>170357.8956<br>170357.8956 |
| 3) The values of B in radians for each peak 0.001607724878, 0.004823174635, 0.004823174635, 0.002411587318, 0.001607724878, 0.003215449757, 0.003215449757 | 4 4 0<br>4 4 0 | | 107635.3685<br>107635.3685 |
| 4) The Miller indices of XRD peaks [h, k, l] [2 1 1], [2 2 2], [4 0 0], [4 1 1], [3 3 2], [4 3 1], [4 4 0] | | | |
| 5) Unit Cell Parameters (a, b, c, α, β, γ) a = b = c = 10.116 Å, α = β = γ = 90° | 3) Crystal shape generated is illustrated in FIG. 18. | | |

This corresponds to the XRD data of $In_2O_3$ nanocrystal which belongs to the cubic system. The crystal shape algorithm has computed 6 exposed faces for this crystal. It is to be noted that each pair of opposite faces have equal areas. The actual crystal shape generated is also shown. The XRD and TEM of $In_2O_3$ are reported in Langmuir 20, 27, 2004.

Figure 19:
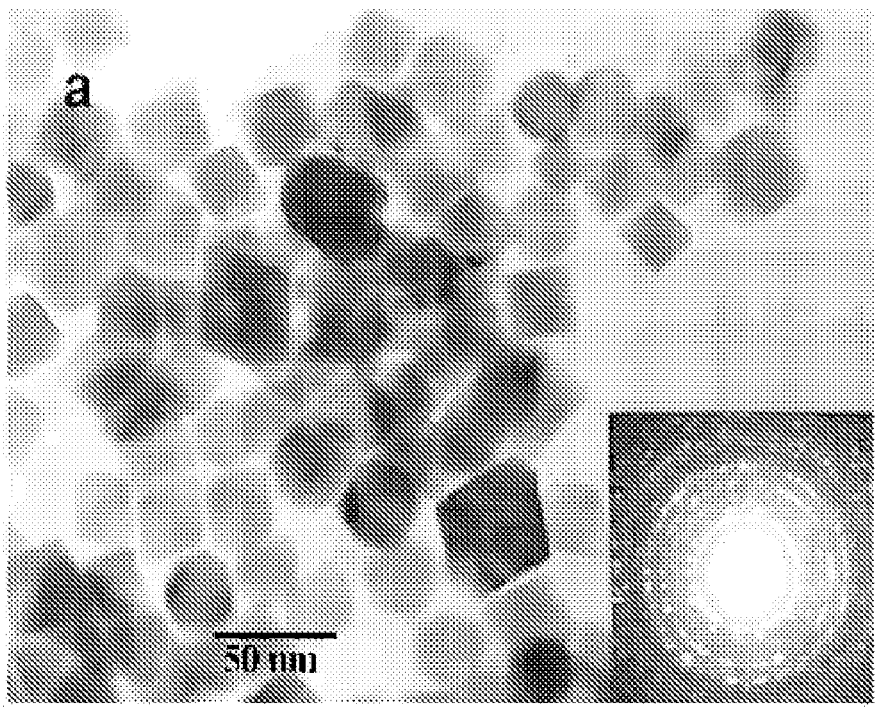
FIG. 19 illustrates a crystal shape of $In_2O_3$ experimentally found using TEM.

FIG. 19 shows the crystal shape of $In_2O_3$ as experimentally found using the transmission electron microscope (TEM). It is evident that most particles have a square or rhombohedral shape, agreeing with the shape generated by our algorithm.

EXAMPLE 13

Crystal Shape Computed from XRD of $Zr_{56}C_{44}$ Crystal

Figure 20:
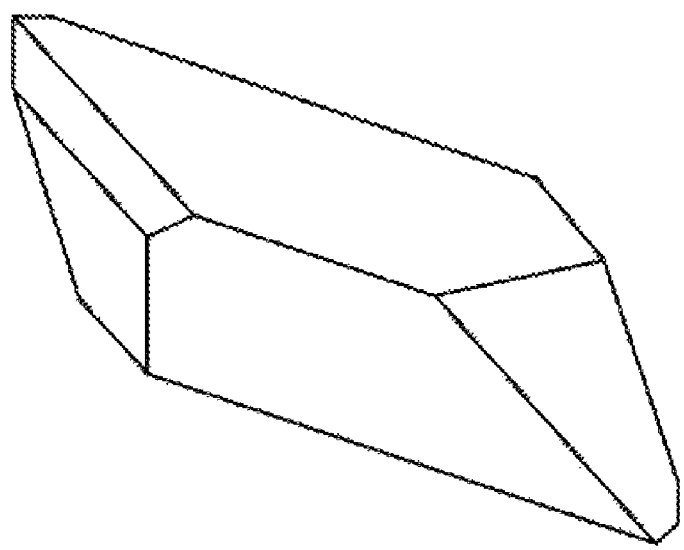
FIG. 20 illustrates a crystal shape computed from XRD data of $Zr_{56}C_{44}$ crystal.

| Inputs to the crystal shape algorithm | Outputs from crystal shape algorithm | | |
|---|---|---|---|
| 1) Number of XRD peaks (n) 8 | 1) Miller indices of the crystal faces exposed [2 0 0], [2 0 0], [2 2 0], [2 2 0], [3 1 1], [3 1 1], [2 2 2], [2 2 2], [3 3 1], [3 3 1], [4 2 0], [4 2 0] | | |
| 2) The values of 2θ in degrees for | Areas of the crystal faces: | | |
| each peak | Crystal face exposed | | Area(Å)$^2$ |
| 31.48936170, 36.70212764, 54.57446807, 65.00000002, 68.72340426, 81.75531915, 91.06382981, 94.78723401 | 2 0 0<br>2 0 0<br>2 2 0<br>2 2 0<br>3 1 1<br>3 1 1 | | 2403.089453<br>2403.089453<br>56.98399609<br>56.98399609<br>1160.241142<br>1160.241142 |
| 3) The values of B in radians for each peak 0.006498566363, 0.01299713273, 0.01299713273, 0.01949569910, 0.03249283183, 0.006498566363, 0.03249283183, 0.05198853093 | 2 2 2<br>2 2 2<br>3 3 1<br>3 3 1 | | 12593.69700<br>12593.69700<br>4507.038566<br>4507.038566 |
| 4) The Miller indices of XRD peaks [h, k, l] [1 1 1], [2 0 0], [2 2 0], [3 1 1], [2 2 2], [4 0 0], [3 3 1], [4 2 0] | 4 2 0<br>4 2 0 | | 14871.39390<br>14871.39390 |
| 5) Unit Cell Parameters (a, b, c, α, β, γ) a = b = c = 4.69302 Å, α = β = γ = 90° | 3) Crystal shape generated is illustrated in FIG. 20. | | |

This corresponds to the XRD data of $Zr_{56}C_{44}$ which exhibits 8 peaks. The crystal shape algorithm has computed 12 exposed faces for this crystal. It is to be noted that each pair of opposite faces have equal areas. The actual crystal shape found is also shown. The XRD and TEM of $Zr_{56}C_{44}$ are reported in Journal of Alloys and compounds 299, 244, 2000.

Figure 21:
FIG. 21 illustrates a crystal shape of $Zr_{56}C_{44}$ experimentally found using TEM.

FIG. 21 shows the crystal shape as experimentally found using the transmission electron microscope (TEM). It is clear from this TEM photograph that the sample exhibits crystallites of different shapes. In such cases, what our math algorithm captures is an average size typical of the specimen. Hence no clear-cut comparison between the computed and experimental shapes is possible.

EXAMPLE 14

Crystal Shape Computed from XRD of $MnFe_2O_4$ Crystal

Figure 22:
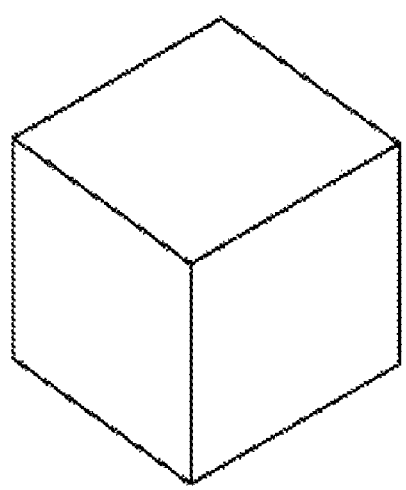
FIG. 22 illustrates a crystal shape computed from XRD data of $MnFe_2O_4$ crystal.

| Inputs to the crystal shape algorithm | Outputs from crystal shape algorithm | | |
|---|---|---|---|
| 1) Number of XRD peaks (n) 3 | 1) Miller indices of the crystal faces exposed [2 2 0], [2 2 0], [3 3 1], [3 3 1], [4 0 0], [4 0 0] | | |
| 2) The values of 2θ in degrees for | Areas of the crystal faces: | | |
| each peak | Crystal face exposed | | Area(Å)$^2$ |
| 35.06493506, 41.18181818, 49.48051947 | 2 2 0<br>2 2 0<br>3 3 1<br>3 3 1 | | 16840.74459<br>16840.74459<br>21256.57522<br>21256.57522 |
| 3) The values of B in radians for each peak 0.02379994436, 0.03059992844, 0.0135999682 | 4 0 0<br>4 0 0 | | 9165.787019<br>9165.787019 |
| 4) The Miller indices of XRD peaks [h, k, l] [2 2 0], [3 1 1], [4 0 0] | | | |
| 5) Unit Cell Parameters (a, b, c, α, β, γ) a = b = 8.519 Å, c: = 8.54 Å; α = β = γ = 90° | 3) Crystal shape generated is illustrated in FIG. 22. | | |

This corresponds to the XRD data of $MnFe_2O_4$ which exhibits 3 peaks and belongs to the tetragonal system. The crystal shape algorithm has computed 6 exposed faces for this crystal. It is to be noted that each pair of opposite faces have equal areas. The actual crystal shape found is also shown. The XRD and TEM of $MnFe_2O_4$ are reported in J. Am. Chem. Soc. 126, 11458, 2004.

Figure 23:
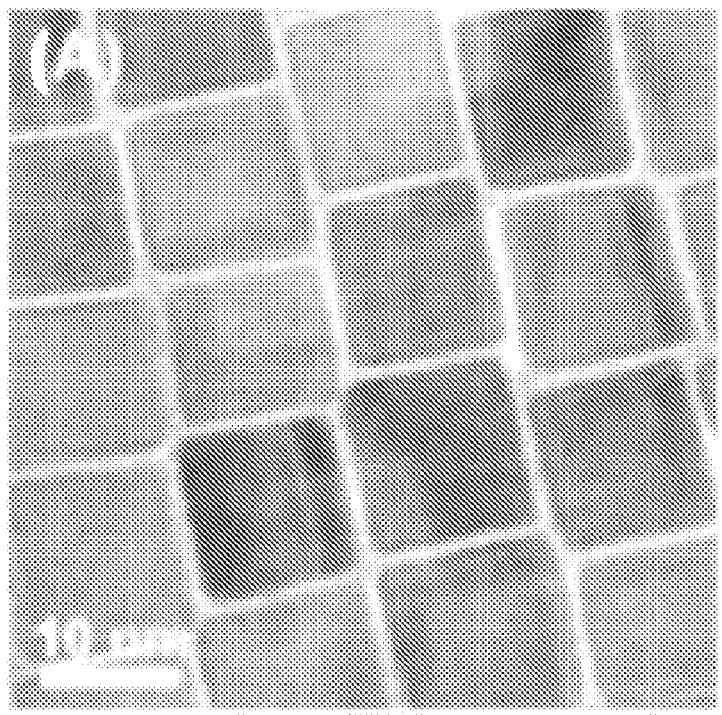
FIG. 23 illustrates a crystal shape of $MnFe_2O_4$ experimentally found using TEM.

FIG. 23 shows the crystal shape as experimentally found using the transmission electron microscope (TEM). The present mathematical algorithm generates a cubelike crystal shape which shows excellent agreement with the TEM photograph. Note that the crystals have identical shapes and nearly the same sizes.

EXAMPLE 15

Crystal Shape Computed from XRD of ZnO Crystal

Figure 24:
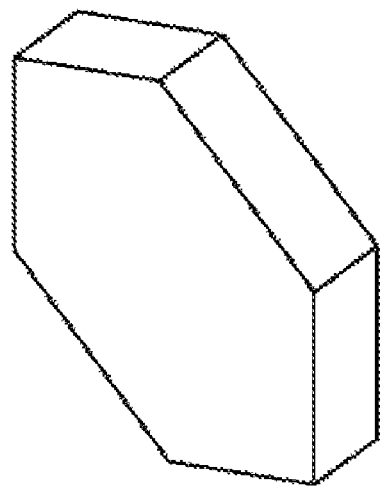
FIG. 24 illustrates a crystal shape computed from XRD data of ZnO crystal.

| Inputs to the crystal shape algorithm | Outputs from crystal shape algorithm | |
|---|---|---|
| 1) Number of XRD peaks (n) 5 | 1) Miller indices of the crystal faces exposed | |
| | [1 0 0], [1 0 0], [0 0 2], [0 0 2], | |
| | [1 0 2], [1 0 2], [1 1 0], [1 1 0] | |
| 2) The values of 2θ in degrees for | Areas of the crystal faces: | |
| each peak | Crystal face exposed | Area(Å)² |
| 31.85950415, 34.46280992, | 1 0 0 | 41100.86716 |
| 36.44628098, 47.72727272, | 1 0 0 | 41100.86716 |
| 56.52892562 | 0 0 2 | 37285.88642 |
| 3) The values of B in radians for each | 0 0 2 | 37285.88642 |
| peak | 1 0 2 | 56951.06674 |
| 0.004327262608, 0.004327262608, | 1 0 2 | 56951.06674 |
| 0.00432726208, 0.006490893912, | 1 1 0 | 137906.5080 |
| 0.006490893912 | 1 1 0 | 137906.5080 |
| 4) The Miller indices of XRD peaks | | |
| [h, k, l] | | |
| [1 0 0], [0 0 2], [1 0 1] | | |
| [1 0 2], [1 1 0] | | |
| 5) Unit Cell Parameters | 3) Crystal shape generated is | |
| (a, b, c, α, β, γ) | illustrated in FIG. 24. | |
| a = b = 3.242 Å, c = 5.176 Å α = β = 90°, γ = 120° | | |

This example corresponds to the XRD data of ZnO which exhibits 5 peaks and belongs to the hexagonal system. The crystal shape algorithm has computed 8 exposed faces for this crystal. It is to be noted that each pair of opposite faces have equal areas. The actual crystal shape found is also shown. The XRD and TEM of ZnO are reported in Materials Science and Engineering B, 111, 197, 2004

Figure 25:
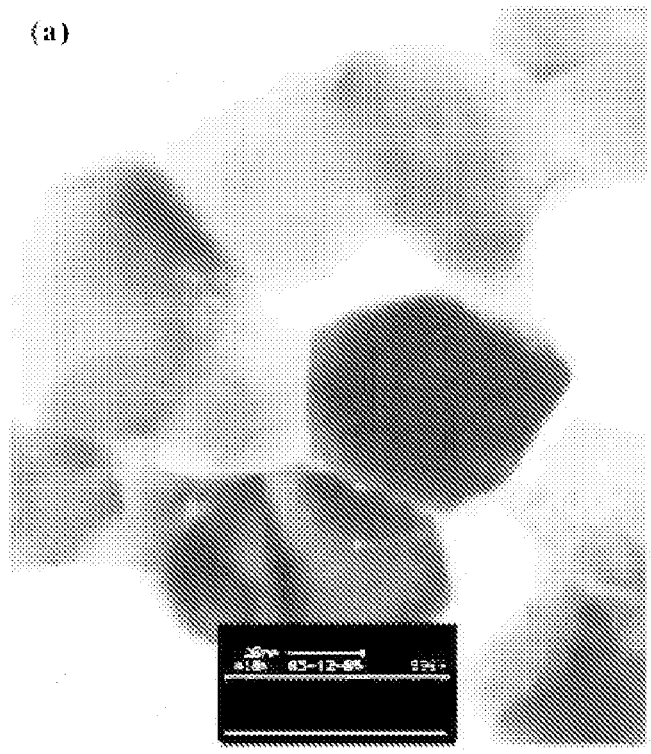
FIG. 25 illustrates a crystal shape of ZnO experimentally found using TEM.

FIG. 25 shows typical TEM photographs of nearly hexagonal nanocrystalline ZnO particle. Though one or two crystals are distorted from the perfect hexagonal shape, the over-all agreement with the computed crystal shape is evident. Note that the two crystals which cut the picture frame at the lower right corner indeed possess the hexagonal shape.

EXAMPLE 16

Crystal Shape Computed from XRD of Fe(II-III) Hydroxysulphate Crystal

Figure 26:
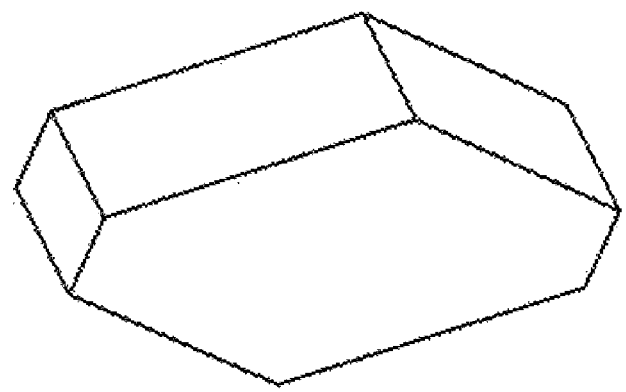
FIG. 26 illustrates a crystal shape computed from XRD data of Fe(II-III) hydroxyl sulphate crystal.

| Inputs to the crystal shape algorithm | Outputs from crystal shape algorithm | |
|---|---|---|
| 1) Number of XRD peaks (n) 7 | 1) Miller indices of the crystal faces exposed | |
| | [1 1 0], [1 1 0], [1 0 4], [1 0 4], | |
| | [0 0 5], [0 0 5], [1 0 1], [1 0 1] | |
| 2) The values of 2θ in degrees for | Areas of the crystal faces: | |
| each peak | Crystal face exposed | Area(Å)² |
| 6.788990826, 12.75229358, | 1 1 0 | 28802.88853 |
| 20.50458716, 27.66055046, | 1 1 0 | 28802.88853 |
| 32.43119265, 36.00917431, | 1 0 4 | 12563.72497 |
| 37.20183488 | 1 0 4 | 12563.72497 |
| 3) The values of B in radians for each | 0 0 5 | 6015.346970 |
| peak | 0 0 5 | 6015.346970 |
| 0.02081585346, 0.01040792673, | 1 0 1 | 3337.466289 |
| 0.02081585346, 0.01040792673, | 1 0 1 | 3337.466289 |
| 0.01040792673, 0.01040792673, | | |
| 0.01040792673 | | |
| 4) The Miller indices of XRD peaks | | |
| [h, k, l] | | |
| [1 1 0], [1 0 5], [1 0 4], | | |
| [0 0 5], [1 0 2], [1 0 1], | | |
| [0 0 4] | | |
| 5) Unit Cell Parameters | 3) Crystal shape generated is | |
| (a, b, c, α, β, γ) | illustrated in FIG. 26. | |
| a = b = 3.18 Å, c = 10.9 Å α = β = 90°, γ = 120° | | |

This corresponds to the XRD data of Fe(II-III)hydroxysulphate which belongs to the hexagonal system. The crystal shape algorithm has computed 8 exposed faces for this crystal. It is to be noted that each pair of opposite faces have equal areas. The actual crystal shape found is also shown. The XRD and TEM of Fe(II-III) hydroxysulphate are reported in Solid State Science 4, 61, 2002.

Figure 27:
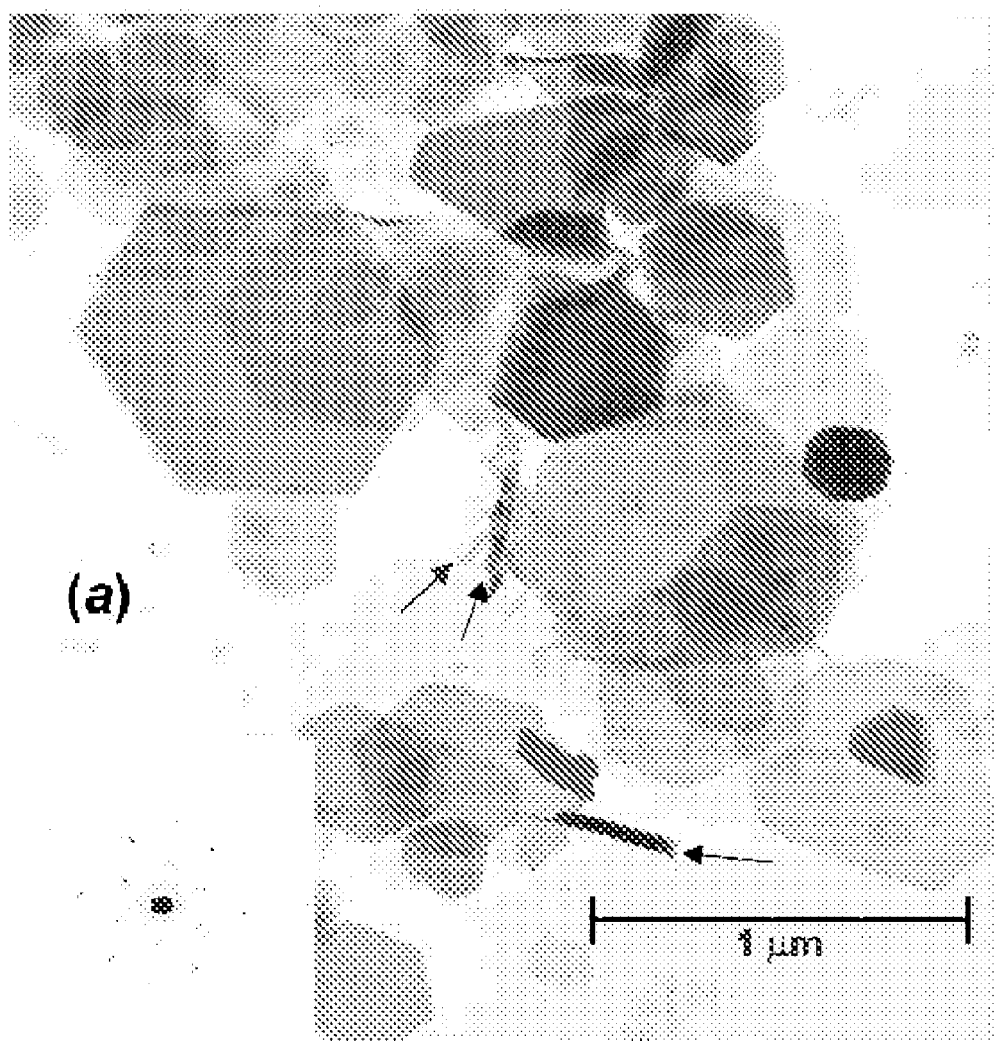
FIG. 27 illustrates a crystal shape of Fe(II-III) hydroxyl sulphate experimentally found using TEM.

FIG. 27 shows the crystal shape as experimentally found using the transmission electron microscope (TEM). The present mathematical algorithm generates a hexagonal crystal shape which agrees well with the TEM photograph.

ADVANTAGES

Depending on the embodiment, advantages of the present invention may include:

1. The shapes/habits/morphologies of the crystals present in the material specimen can be generated from the XRD of the specimen.
2. One gets quantitative information while the prior-art equipments such as TEM and HRTEM yield only visual photographs.
3. Another advantage of one embodiment of the present invention is that it enables experimentalists to find the crystal structure and crystal shape by using one and the same equipment, viz. XRD.
4. In one embodiment a unique miller index (h, k, l) is assigned to each of the crystal faces identified.
5. Three dimensional information is possible whereas hitherto only projected two dimensional information was accessible to prior-art.

6. Crystal shapes can be viewed from arbitrary angles.
7. Generation of crystal shapes will be cheaper using the said algorithmic process.
8. One and the same instrument, viz. x-ray diffractometer, can be used to generate both the internal structure and the external shape of crystals.
9. The algorithm is superbly suited to find the crystal shapes of nano-crystal and materials.
10. Any crystalline, i.e., non-amorphous, material specimen can be subjected to the said process. The material can be in a powder form or in a single crystal form. The material may further belong to any of the 7 crystal systems (Triclinic, Monoclinic, Orthorhombic, Trigonal, Tetragonal, Hexagonal and Cubic; see Table 1 for further details).

What is claimed is:

1. A method of computing crystal shapes from X-Ray Diffraction Data (XRD) of a substance, the method comprising:
   a) obtaining input parameters associated with said substance, said parameters comprising:
      (i) number of XRD peaks (n),
      (ii) (2·θ), wherein θ represents the angle of incidence on said substance of X-rays, and
      (iii) the peak-width at half maximum, represented as B, for each of the XRD peaks;
   b) indexing by assigning the Miller indices (h, k, l) to each of the XRD peaks;
   c) determining at least one unit cell parameter associated with said substance;
   d) determining crystal thickness associated with said substance in different directions based at least in part on the data gathered from step (a) and step (b) in Scherrer formula ($t_{hkl}=0.9\lambda/B \cos\theta_{hkl}$), wherein $\lambda$, represents the wavelength of said X-rays, $\theta_{hkl}$ represents angle of incidence of X-rays on the planes having Miller indices (h, k, l), and $t_{hkl}$ represents a thickness of crystal perpendicular to said (h, k, l) planes;
   e) based at least partly on the data gathered from steps (a) to (d), determining using a processor a set of crystal planes which determine the mathematical envelope for the crystal shape associated with said substance, wherein said crystal planes are associated with crystal faces;
   f) determining co-ordinates of each point of intersection of said crystal planes;
   g) determining a set of all real points of intersection;
   h) for each of said crystal planes, identifying a set of real points of intersection which fall on said plane;
   i) transforming using the processor coordinates of said real points of intersection from Global to Local frames, wherein said real points of intersection are associated with vertices of said crystal faces;
   j) determining using the processor a polar co-ordinate [$\theta_i$] of each of the vertices ordered in an ascending series in each of the crystal faces;
   k) determining using the processor a transformation, represented by T, which reshuffles the indices;
   l) based at least partly on the transformation T obtained from step (k), ordering using the processor the vertices on each crystal plane and computing the areas and Miller indices of exposed crystal faces; and
   m) determining using the processor a 3D crystal shape associated with said substance.

2. The method of claim 1, wherein determining a 3D crystal shape associated with said substance further comprises generating the external shape of crystals associated with said substance.

3. The method of claim 1, wherein determining a 3D crystal shape further comprises determining the crystal shapes from arbitrary angles.

4. The method of claim 1, wherein determining a 3D crystal shape associated with said substance further comprises determining crystal shapes of nano crystals.

5. The method of claim 1, wherein determining a 3D crystal shape associated with said substance further comprises determining the crystal shapes of nano materials.

6. The method of claim 1, wherein determining a 3D crystal shape further comprises determining a 3D crystal shape associated with seven crystal systems.

7. The method of claim 1, wherein determining a 3D crystal shape further comprises determining a 3D crystal shape associated with a powder specimen.

8. The method of claim 1, wherein determining a 3D crystal shape further comprises determining at least one of a Triclinic, Monoclinic, Orthorhombic, Trigonal, Tetragonal, Hexagonal, or Cubic crystal shape.

9. A system for computing crystal shapes from X-Ray Diffraction Data (XRD) of a substance, the system comprising:
   a memory configured to store parameters associated with said substance, said parameters comprising:
      number of XRD peaks (n),
      (2·θ), wherein θ represents the angle of incidence on said substance of X-rays, and
      the peak-width at half maximum, represented as B, for each of the XRD peaks;
   a processor configured to:
      index by assigning the Miller indices (h, k, l) to each of the XRD peaks;
      determine at least one unit cell parameter associated with said substance;
      determine crystal thickness associated with said substance in different directions based at least in part on the data gathered from step (a) and step (b) in Scherrer formula ($t_{hkl}=0.9\lambda/B \cos\theta_{hkl}$), wherein $\lambda$ represents the wavelength of said X-rays, $\theta_{hkl}$ represents angle of incidence of X-rays on the planes having Miller indices (h, k, l), and $t_{hkl}$ represents a thickness of crystal perpendicular to said (h, k, l) planes;
      based at least partly on the data gathered from steps (a) to (d), determine a set of crystal planes which determine the mathematical envelope for the crystal shape associated with said substance, wherein said crystal planes are associated with crystal faces;
      determine co-ordinates of each point of intersection of said crystal planes;
      determine a set of all real points of intersection;
      for each of said crystal planes, identify a set of real points of intersection which fall on said plane;
      transform coordinates of said real points of intersection from Global to Local frames, wherein said real points of intersection are associated with vertices of said crystal faces;
      determine a polar co-ordinate [$\theta_i$] of each of the vertices ordered in an ascending series in each of the crystal faces;
      determine a transformation, represented by T, which reshuffles the indices;
      based at least partly on the transformation T obtained from step (k), order the vertices on each crystal plane and computing the areas and Miller indices of exposed crystal faces; and
      determine a 3D crystal shape associated with said substance.

10. The system of claim 9, comprising an X-ray diffractometer.

11. The system of claim 9, wherein the processor is configured to determine a 3D crystal shape associated with said substance at least by generating the external shape of crystals associated with said substance.

12. The system of claim 9, wherein the processor is configured to determine a 3D crystal shape further by determining the crystal shapes from arbitrary angles.

13. The system of claim 9, wherein the processor is configured to determine a 3D crystal shape associated with said substance by determining crystal shapes of nano crystals.

14. The system of claim 9, wherein the processor is configured to determine a 3D crystal shape associated with said substance further by determining the crystal shapes of nano materials.

15. The system of claim 9, wherein the processor is configured to determine a 3D crystal shape by determining a 3D crystal shape associated with seven crystal systems.

16. The system of claim 9, wherein the processor is configured to determining a 3D crystal shape by determining a 3D crystal shape associated with a powder specimen.

17. The system of claim 9, wherein the processor is configured to determining a 3D crystal shape by determining at least one of a Triclinic, Monoclinic, Orthorhombic, Trigonal, Tetragonal, Hexagonal, or Cubic crystal shape.

18. A computer readable medium having stored thereon instructions that when executed cause a processor to perform a method of computing crystal shapes from X-Ray Diffraction Data (XRD) of a substance, the method comprising:
   a) obtaining input parameters associated with said substance, said parameters comprising:
      (i) number of XRD peaks (n),
      (ii) (2·θ), wherein θ represents the angle of incidence on said substance of X-rays, and
      (iii) the peak-width at half maximum, represented as B, for each of the XRD peaks;
   b) indexing by assigning the Miller indices (h, k, l) to each of the XRD peaks;
   c) determining at least one unit cell parameter associated with said substance;
   d) determining crystal thickness associated with said substance in different directions based at least in part on the data gathered from step (a) and step (b) in Scherrer formula ($t_{hkl}=0.9\lambda/B \cos \theta_{hkl}$), wherein $\lambda$ represents the wavelength of said X-rays, $\theta_{hkl}$ represents angle of incidence of X-rays on the planes having Miller indices (h, k, l), and $t_{hkl}$ represents a thickness of crystal perpendicular to said (h, k, l) planes;
   e) based at least partly on the data gathered from steps (a) to (d), determining a set of crystal planes which determine the mathematical envelope for the crystal shape associated with said substance, wherein said crystal planes are associated with crystal faces;
   f) determining co-ordinates of each point of intersection of said crystal planes;
   g) determining a set of all real points of intersection;
   h) for each of said crystal planes, identifying a set of real points of intersection which fall on said plane;
   i) transforming coordinates of said real points of intersection from Global to Local frames, wherein said real points of intersection are associated with vertices of said crystal faces;
   j) determining a polar co-ordinate [θi] of each of the vertices ordered in an ascending series in each of the crystal faces;
   k) determining a transformation, represented by T, which reshuffles the indices;
   l) based at least partly on the transformation T obtained from step (k), ordering the vertices on each crystal plane and computing the areas and Miller indices of exposed crystal faces; and
   m) determining a 3D crystal shape associated with said substance.

* * * * *